US 12,004,932 B2

(12) United States Patent
Erdem et al.

(10) Patent No.: US 12,004,932 B2
(45) Date of Patent: Jun. 11, 2024

(54) APERTURED NONWOVEN WEBS

(71) Applicant: The Procter & Gamble Company, Cincinnati, OH (US)

(72) Inventors: Gueltekin Erdem, Beijing (CN); Meng Chen, Beijing (CN); Jihua Xie, Xiamen (CN); Jixiang Cai, Xiamen (CN)

(73) Assignee: The Procter & Gamble Company, Cincinnati, OH (US)

( * ) Notice: Subject to any disclaimer, the term of this patent is extended or adjusted under 35 U.S.C. 154(b) by 531 days.

(21) Appl. No.: 16/919,541

(22) Filed: Jul. 2, 2020

(65) Prior Publication Data

US 2021/0015685 A1    Jan. 21, 2021

(30) Foreign Application Priority Data

Jul. 16, 2019 (WO) ................ PCT/CN2019/096067

(51) Int. Cl.
*A61F 13/512* (2006.01)
*A61F 13/15* (2006.01)
(Continued)

(52) U.S. Cl.
CPC .... *A61F 13/5123* (2013.01); *A61F 13/15699* (2013.01); *A61F 13/5116* (2013.01);
(Continued)

(58) Field of Classification Search
CPC ........... A61F 13/5123; A61F 13/15699; A61F 13/5116; A61F 2013/51178; A61F 2013/53035
See application file for complete search history.

(56) References Cited

U.S. PATENT DOCUMENTS 4,588,630 A    5/1986 Shimalla
5,628,097 A    5/1997 Benson et al.
(Continued)

FOREIGN PATENT DOCUMENTS

CN    1476317 A    2/2004
CN    2764341 Y    3/2006
(Continued)

OTHER PUBLICATIONS

Corrected International Search Report and Written Opinion; Application Ser. No. PCT/CN2019/096067; dated Apr. 27, 2020; 10 pages.
(Continued)

*Primary Examiner* — Jessica Arble
(74) *Attorney, Agent, or Firm* — Daniel S. Albrecht; Christian M. Best

(57) ABSTRACT

An apertured nonwoven web is provided. The apertured nonwoven web comprises carded fibers, a first side, and a second side. The apertured nonwoven web defines a plurality of apertures therein. The apertures may each have a first side aperture size and a second side aperture size, and a ratio of the first side aperture size to the second side aperture size may be between about 1.15:1 to about 1:1.15. The plurality of apertures may have an aperture size regularity of about 1% to about 15%. The plurality of apertures may have an aperture shape regularity between about 1% to about 12%.

20 Claims, 21 Drawing Sheets

(51) Int. Cl.
*A61F 13/511* (2006.01)
*A61F 13/53* (2006.01)
(52) U.S. Cl.
CPC .............. *A61F 2013/51178* (2013.01); *A61F 2013/53035* (2013.01)

(56) References Cited

U.S. PATENT DOCUMENTS

| | | |
|---|---|---|
| 6,610,391 B2 | 8/2003 | Molee |
| 6,645,190 B1 | 11/2003 | Olson et al. |
| 6,761,711 B1 | 7/2004 | Fletcher et al. |
| 6,817,994 B2 | 11/2004 | Popp et al. |
| 6,840,928 B2 | 1/2005 | Datta et al. |
| 6,849,067 B2 | 2/2005 | Fletcher et al. |
| 6,893,426 B1 | 5/2005 | Popp et al. |
| 6,953,452 B2 | 10/2005 | Popp et al. |
| 6,969,377 B2 | 11/2005 | Koele et al. |
| 7,118,639 B2 | 10/2006 | Delucia et al. |
| 7,156,833 B2 | 1/2007 | Couture-Dorschner et al. |
| 7,201,744 B2 | 4/2007 | Van Gompel et al. |
| 7,497,851 B2 | 3/2009 | Koele et al. |
| 7,682,349 B2 | 3/2010 | Popp et al. |
| 7,862,550 B2 | 1/2011 | Koele et al. |
| 7,935,861 B2 | 5/2011 | Suzuki |
| 8,007,485 B2 | 8/2011 | Popp et al. |
| 8,361,048 B2 | 1/2013 | Kuen et al. |
| 8,372,052 B2 | 2/2013 | Popp et al. |
| 8,579,876 B2 | 11/2013 | Popp et al. |
| 8,747,379 B2 | 6/2014 | Fletcher et al. |
| 9,421,137 B2 | 8/2016 | Lavon |
| 2002/0187322 A1 | 12/2002 | Molee |
| 2003/0105190 A1 | 6/2003 | Diehl et al. |
| 2004/0087927 A1 | 5/2004 | Suzuki |
| 2005/0228353 A1 | 10/2005 | Thomas |
| 2006/0128245 A1 | 6/2006 | Muth |
| 2012/0100350 A1 | 4/2012 | Shim |
| 2013/0211363 A1 | 8/2013 | LaVon et al. |
| 2014/0005020 A1 | 1/2014 | LaVon et al. |
| 2015/0083310 A1* | 3/2015 | Wade ................. A61F 13/4902 156/167 |
| 2016/0136014 A1 | 5/2016 | Arora et al. |
| 2016/0167334 A1* | 6/2016 | Arora ................. A61F 13/5116 428/137 |
| 2016/0287450 A1 | 10/2016 | Andersson |
| 2017/0112688 A1 | 4/2017 | Amano |
| 2017/0246044 A1 | 8/2017 | Ludwig |
| 2017/0246052 A1 | 8/2017 | Ludwig |
| 2017/0246053 A1 | 8/2017 | Ludwig |
| 2017/0348165 A1 | 12/2017 | Grenier |
| 2018/0000656 A1 | 1/2018 | Roe |
| 2018/0344539 A1 | 12/2018 | Kurihara |
| 2018/0360671 A1 | 12/2018 | Joseph |

FOREIGN PATENT DOCUMENTS

| | | |
|---|---|---|
| CN | 101818415 A | 9/2010 |
| CN | 201686823 U | 12/2010 |
| CN | 102673030 A | 9/2012 |
| CN | 202537784 U | 11/2012 |
| CN | 103565589 B | 11/2015 |
| CN | 105208988 A | 12/2015 |
| CN | 105496657 A | 4/2016 |
| CN | 106176058 A | 12/2016 |
| CN | 106535846 A | 3/2017 |
| CN | 107460634 A | 12/2017 |
| CN | 107485490 A | 12/2017 |
| CN | 108778706 A | 11/2018 |
| CN | 106811866 B | 3/2019 |
| JP | 3090669 B2 | 10/1989 |
| JP | H1189879 A | 4/1999 |
| JP | 2002238946 A | 8/2002 |
| JP | 5463080 B2 | 1/2014 |
| JP | 6100655 B2 | 3/2017 |
| WO | WO02091971 A1 | 11/2002 |
| WO | WO2004007158 A1 | 1/2004 |
| WO | WO2010032951 A3 | 7/2010 |
| WO | 2012174025 A2 | 12/2012 |
| WO | WO2013042501 A1 | 3/2013 |
| WO | WO2015084221 A1 | 6/2015 |
| WO | WO2017094756 A1 | 6/2017 |
| WO | 2017171775 A1 | 10/2017 |

OTHER PUBLICATIONS

PCT International Search Report, dated Mar. 26, 2020, 11 pages.
PCT Supplementary International Search Report Or Declaration for PCT/CN2019/096067 dated Oct. 26, 2021, 7 pages.

* cited by examiner

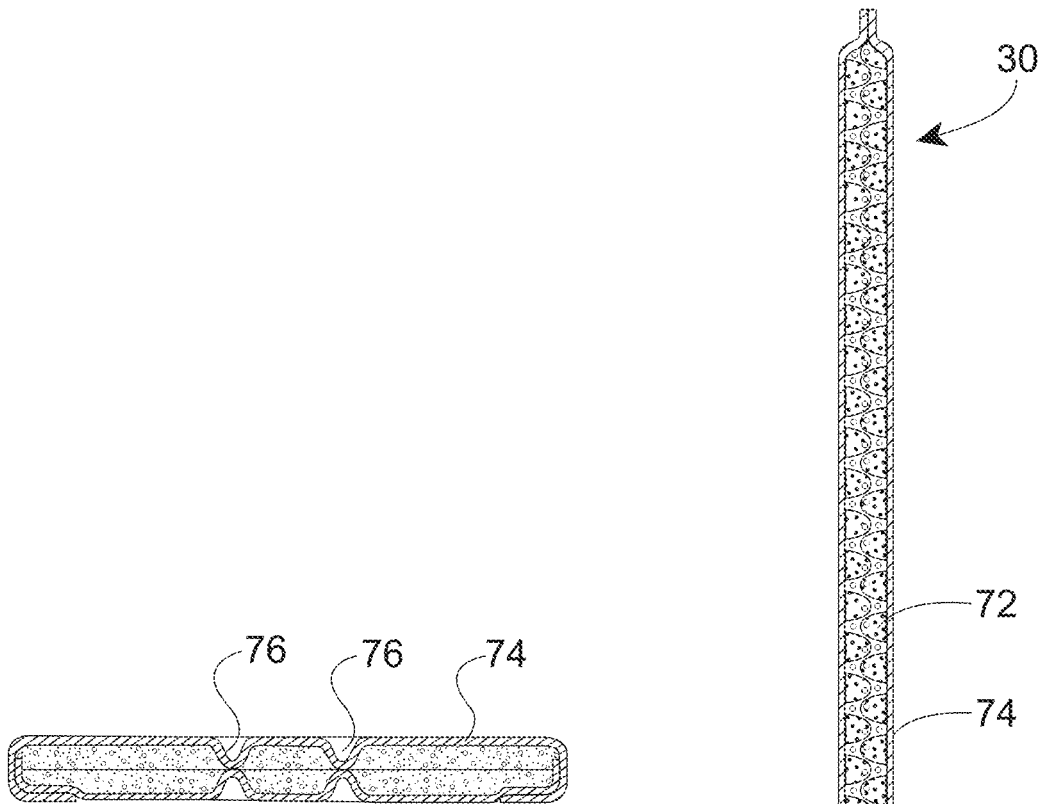
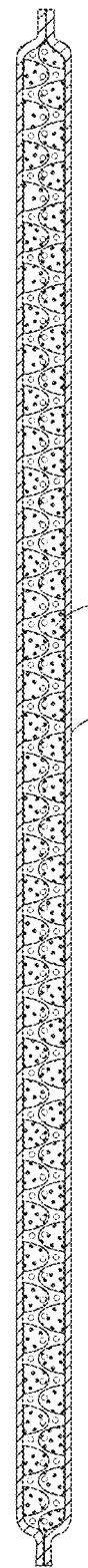
Fig. 10
Fig. 11

APERTURED NONWOVEN WEBS

CROSS REFERENCE TO RELATED APPLICATIONS

This application is a continuation of, and claims priority under 35 U.S.C. § 120 to, International Patent Application No. PCT CN2019/096067, filed on Jul. 16, 2019, the entire disclosure of which is hereby incorporated by reference.

FIELD

The present disclosure is generally directed to apertured nonwoven webs. The apertured nonwoven webs of the present disclosure may be used in absorbent articles, for example as topsheets, portions of belts, outer cover nonwoven materials, or other absorbent article components.

BACKGROUND

Nonwoven webs are useful in many fields, such as the medical field, the dusting and cleaning implement field, and the hygiene field, for example. In the hygiene field, absorbent articles, such as diapers, training pants, sanitary napkins, and adult incontinence products, may be used to absorb and contain urine, bowel movements, and/or menses (together "bodily exudates"). These absorbent articles may comprise nonwoven webs as various components thereof. Some example components that use nonwoven webs are topsheets, acquisition materials, outer cover nonwoven materials, and/or portions of belts, for example. The topsheet is one component of an absorbent article that contacts the skin of a wearer. Frequently, nonwoven topsheets are apertured to aid in bodily exudate acquisition, especially in a wearer-facing hydrophobic topsheet layer or full hydrophobic topsheet context. In some instances, it may be desirable to have apertures having the same, or substantially similar, aperture areas and/or aperture sizes throughout the topsheet to ensure uniform bodily exudate acquisition. However, conventional aperturing processes (e.g., hot pin aperturing, water-jet punching, and over-bonding and ring-rolling) applied to nonwoven webs may result in irregular aperture patterns, non-uniform aperture shapes and sizes, reduced clarity of the apertures caused by stray fibers extending across, or partially across, the apertures, and formation of hydrophobic aperture perimeter tails that project into a hydrophilic acquisition layer or other layers under a topsheet. All these items may lead to less than desired bodily exudate acquisition and reduced visual quality of the topsheet. One solution may be to increase the size of the apertures. Such a solution, however, may lead to a loss of tactile softness, reduced visual appeal, and a topsheet with reduced strength that is easily deformed and difficult to convert during absorbent article manufacturing operations. As such, nonwoven apertured topsheets should be improved.

SUMMARY

Aspects of the present disclosure solve the problems discussed above by providing nonwoven webs with apertures having more uniform aperture areas and/or aperture sizes and/or having improved aperture clarity (e.g., less fibers extending across, or partially across the apertures). The apertures defined in the nonwoven webs or topsheets of the present disclosure having less, or hardly any, stray fibers extending therethrough or thereacross may lead to improved bodily exudate acquisition, especially in a hydrophobic nonwoven topsheet context. If a hydrophobic fiber or fibers extend(s) across, or partially across, an aperture, this may effectively reduce the size of the aperture to, for example, half of its size, and may impede bodily exudate acquisition by providing an aperture opening that is too small to overcome the surface tension of the bodily exudate. The apertures of the present disclosure may also be free of or have reduced aperture perimeter tails, leading to improved bodily exudate acquisition since fibers of a hydrophilic acquisition material below the topsheet may be able to come into contact with or partially extend into the apertures. Further, aperture perimeter tails may be hydrophobic in that they are extensions of a hydrophobic topsheet, thereby potentially partially blocking contact with the hydrophilic acquisition material below the topsheet.

BRIEF DESCRIPTION OF THE DRAWINGS

The above-mentioned and other features and advantages of the present disclosure, and the manner of attaining them, will become more apparent and the disclosure itself will be better understood by reference to the following description of example forms of the disclosure taken in conjunction with the accompanying drawings, wherein:

FIG. 10 is a cross-sectional view of the absorbent core, taken about line 10-10 of FIG. 9;

FIG. 11 is a cross-sectional view of the absorbent core, taken about line 11-11 of FIG. 9;

DETAILED DESCRIPTION

Figure 1:
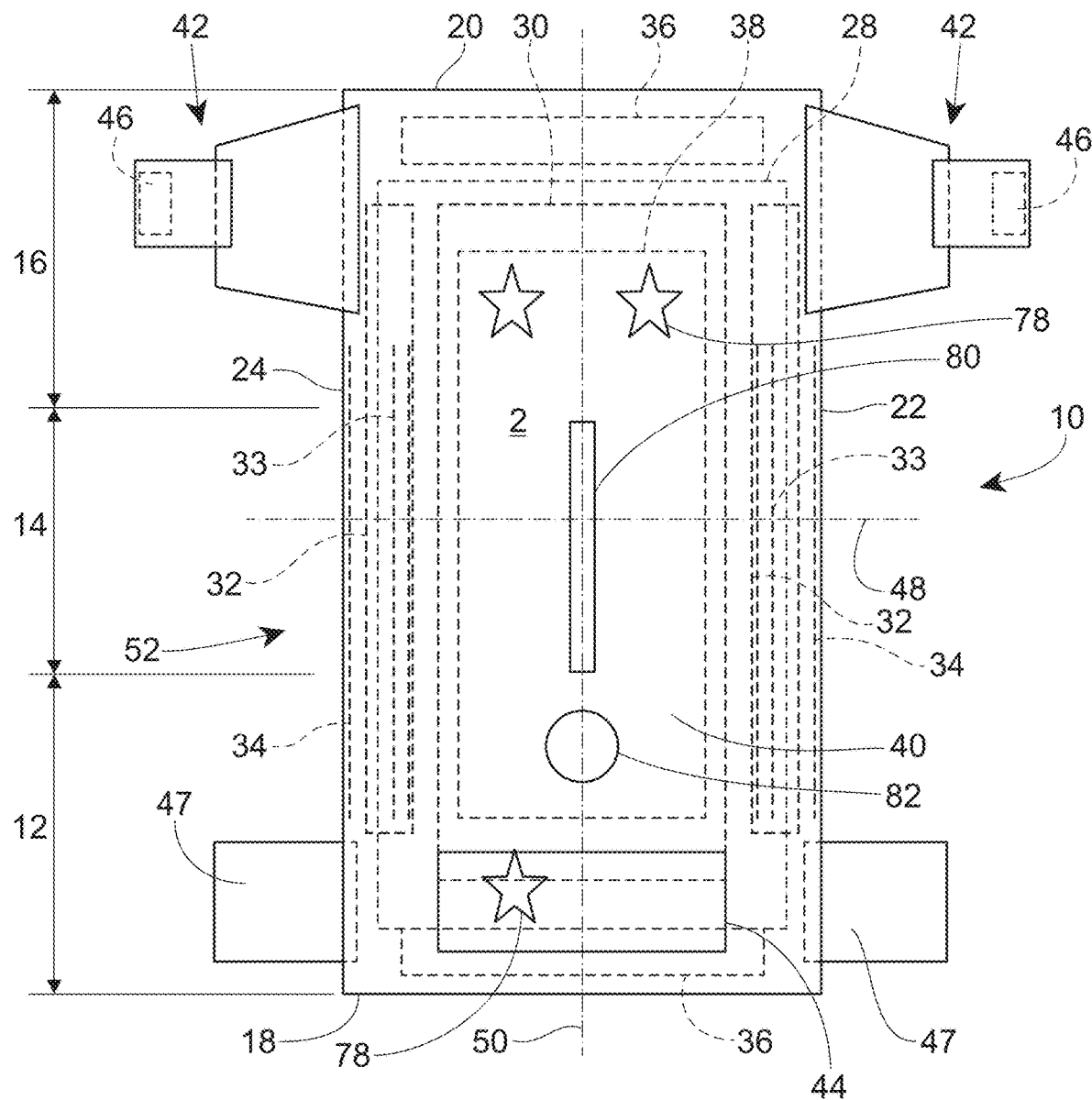
FIG. 1 is a plan view of an example absorbent article in the form of a taped diaper, garment-facing surface facing the viewer, in a flat laid-out state.

Various non-limiting forms of the present disclosure will now be described to provide an overall understanding of the principles of the structure, function, manufacture, and use of the apertured nonwoven webs disclosed herein. One or more examples of these non-limiting forms are illustrated in the accompanying drawings. Those of ordinary skill in the art will understand that the apertured nonwoven webs described herein and illustrated in the accompanying drawings are non-limiting example forms. The features illustrated or described in connection with one non-limiting form may be combined with the features of other non-limiting forms. Such modifications and variations are intended to be included within the scope of the present disclosure.

Definitions

As used herein, the terms "aperture perimeter tail" or "aperture perimeter tails" refers to a portion of a nonwoven web that has been relocated in the web in order to create an aperture, but that remains partially attached to the nonwoven web at a perimeter of the aperture. When an apertured nonwoven web containing aperture perimeter tails is utilized as a topsheet, the aperture perimeter tail may extend into an acquisition material or an absorbent core, pushing down on the acquisition material or the absorbent core, and causing a physical separation of the topsheet and the acquisition material or the absorbent core. This may interrupt wicking of bodily exudates from the topsheet into the acquisition material or into the absorbent core. Further, the aperture perimeter tails may be hydrophobic, thereby blocking hydrophilic acquisition materials or hydrophilic absorbent cores from properly acquiring the bodily exudates. As such, the presence of aperture perimeter tails may contribute to suboptimal penetration of bodily exudates from the topsheet into the acquisition material or into the absorbent core material.

As used herein, the term "absorbent article" refers to disposable devices such as premature infant, baby, child, or adult incontinence diapers, training pants, absorbent pads, incontinence pants or pads, liners, sanitary napkins, and the like which are placed against or in proximity to the body of the wearer to absorb and contain bodily exudates. Typically, these absorbent articles comprise a topsheet, a backsheet, an absorbent core, optionally an acquisition system (which may be comprised of one or several layers), and typically other components, with the absorbent core normally placed at least partially between the backsheet and the acquisition system or between the topsheet and the backsheet. The absorbent articles may take on any suitable configuration.

As used herein, the terms "hydrophilic" and "hydrophobic" have meanings that are well established in the art with respect to the contact angle of water on the surface of a material. Thus, a material having a water contact angle of greater than about 90 degrees is considered hydrophobic, and a material having a water contact angle of less than about 90 degrees is considered hydrophilic. Compositions which are hydrophobic may increase the contact angle of water on the surface of a material, while compositions which are hydrophilic may decrease the contact angle of water on the surface of a material. Notwithstanding the foregoing, reference to relative hydrophobicity or hydrophilicity between a material and a composition, between two materials, and/or between two compositions, does not imply that the materials or compositions are hydrophobic or hydrophilic. For example, a composition may be more hydrophobic than a material. In such a case, neither the composition nor the material may be hydrophobic; however, the contact angle exhibited by the composition is greater than that of the material. As another example, a composition may be more hydrophilic than a material. In such a case, neither the composition nor the material may be hydrophilic; however, the contact angle exhibited by the composition may be less than that exhibited by the material.

As used herein, the terms "joined" or "bonded" or "attached" encompass configurations whereby an element is directly secured to another element by affixing the element directly to the other element, and configurations whereby an element is indirectly secured to another element by affixing the element to intermediate member(s) which in turn are affixed to the other element.

As used herein, the term "natural fibers" refers to elongated substances produced by plants and animals and comprises animal-based fibers and plant-based fibers. Natural fibers may comprise fibers harvested without any post-harvest treatment step as well as those having a post-treatment step, such as, for example, washing, scouring, and bleaching.

As used herein, the term "nonwoven web" refers to a manufactured sheet, web, or batt of directionally or randomly orientated fibers bonded or otherwise joined together. The fibers may be of natural or man-made origin. Commercially available fibers may come in several different forms, such as short fibers (known as staple or carded) and continuous single fibers (filaments or monofilaments), for example. Nonwoven webs can be formed by many processes such as meltblowing, spunbonding, solvent spinning, electrospinning, carding, and airlaying. The basis weight of nonwoven webs is usually expressed in grams per square meter ($g/m^2$ or gsm). Multi-constituent fibers, such as bicomponent fibers, or any other suitable fibers, may also be used in forming the nonwoven webs.

As used herein, the term "plant-based fibers" comprises both harvested fibers and synthetic fibers that comprise bio-based content. Harvested plant-based fibers may comprise cellulosic matter, such as wood pulp; seed hairs, such as cotton; stem (or bast) fibers, such as flax and hemp; leaf fibers, such as sisal; and husk fibers, such as coconut.

Nonwoven Webs

Nonwoven webs are useful in many fields, such as the hygiene field, the dusting and cleaning implement field, and the medical field, for example. In the hygiene filed, nonwoven webs are used in the absorbent article field, such as use as components in diapers, pants, adult incontinence products, tampons, liners, sanitary napkins, absorbent pads, bed pads, wipes, and various other products. Nonwoven webs may be used in absorbent articles as topsheets, outer cover nonwoven materials, portions of leg cuffs, acquisition materials, core wrap materials, portions of ears and side panels, portions of fastener tabs, portions of belts, and/or secondary topsheets, for example. The nonwoven webs of the present disclosure may have particular application as a topsheet and/or an outer cover nonwoven material.

Nonwoven webs discussed herein may be manufactured from a wide range of materials, including plant-based fibers, natural fibers, and/or synthetic fibers. Fibers comprising the nonwoven webs of the present disclosure may be continuous and/or carded. Continuous fibers are generally longer fibers that are laid down in a random fashion in the nonwoven web, whereas carded fibers are generally shorter and have a decided directional lay within the nonwoven web. The nonwoven webs discussed herein may comprise multi-constituent fibers, such as bi-component fibers or tri-component fibers, mono-component fibers, and/or other fiber types, for example. Multi-constituent fibers, as used herein, means fibers comprising more than one chemical species or material (i.e., multi-component fibers). Bi-component fibers are merely an example of multi-constituent fibers. The fibers may have round, triangular, tri-lobal, or otherwise shaped cross-sections, for example. In a continuous fiber or carded fiber context, it may be desirable to have fibers comprising more than one polymer component, such as bi-component fibers. Often, these two polymer components have different melting temperatures, viscosities, glass transition temperatures, and/or crystallization rates. As the multi-component fibers cool after formation, a first polymer component may solidify and/or shrink at a faster rate than a second polymer component, while the second polymer component may have sufficient rigidity to resist compression along a longitudinal fiber axis. The continuous fibers may then deform and curl up when strain on the fiber is relieved, thereby causing what is known as "crimp" in the fibers. Crimp of the fibers may aid in the softness and loft of a nonwoven web or topsheet, which is consumer desirable.

Bi-component fibers may comprise, for example, a first polymer component having a first melting temperature and a second polymer component having a second melting temperature. The first melting temperature of the first polymer component may be about 5 degrees C. to about 180 degrees C., about 10 degrees C. to about 180 degrees C., or about 30 degrees C. to about 150 degrees C., different than the second melting temperature of the second polymer component, thereby causing crimping of the fibers during cooling, specifically reciting all 0.1 degree C. increments within the specified ranges and all ranges formed therein or thereby. The first and second melting temperatures may differ by at least 5 degrees C., at least 10 degrees C., at least 20 degrees C., at least 25 degrees, at least 40 degrees C., at least 50 degrees C., at least 75 degrees C., at least 100 degrees C., at least 125 degrees C., at least 150 degrees C., but may all differ less than 180 degrees C., for example. A first polymer component may comprise polypropylene and a second polymer component may comprise polyethylene, for example. As another example, a first polymer component may comprise polyethylene and a second polymer component may comprise polyethylene terephthalate. As yet another example, a first polymer component may comprise polyethylene and a second polymer component may comprise polylactic acid. If tri-component fibers are used, at least one polymer component may have a different melting temperature (in the ranges specified above) than a melting temperature of at least one of the other two polymer components.

The fibers may comprise petroleum sourced resins, recycled resins, or bio-sourced resins, such as polylactic acid from Nature Works and polyethylene from Braskem. The fibers may be or may comprise continuous fibers, such as spunbond fibers and melt-blown fibers. Staple fibers, either petroleum-sourced or bio-sourced, such as cotton, cellulous, and/or regenerated cellulous may also be included in a nonwoven web. The multi-constituent fibers, such as bi-component fibers, may comprise sheath/core, side-by-side, islands in the sea, and/or eccentric configurations or may have other configurations.

General Description of an Absorbent Article

Figure 2:
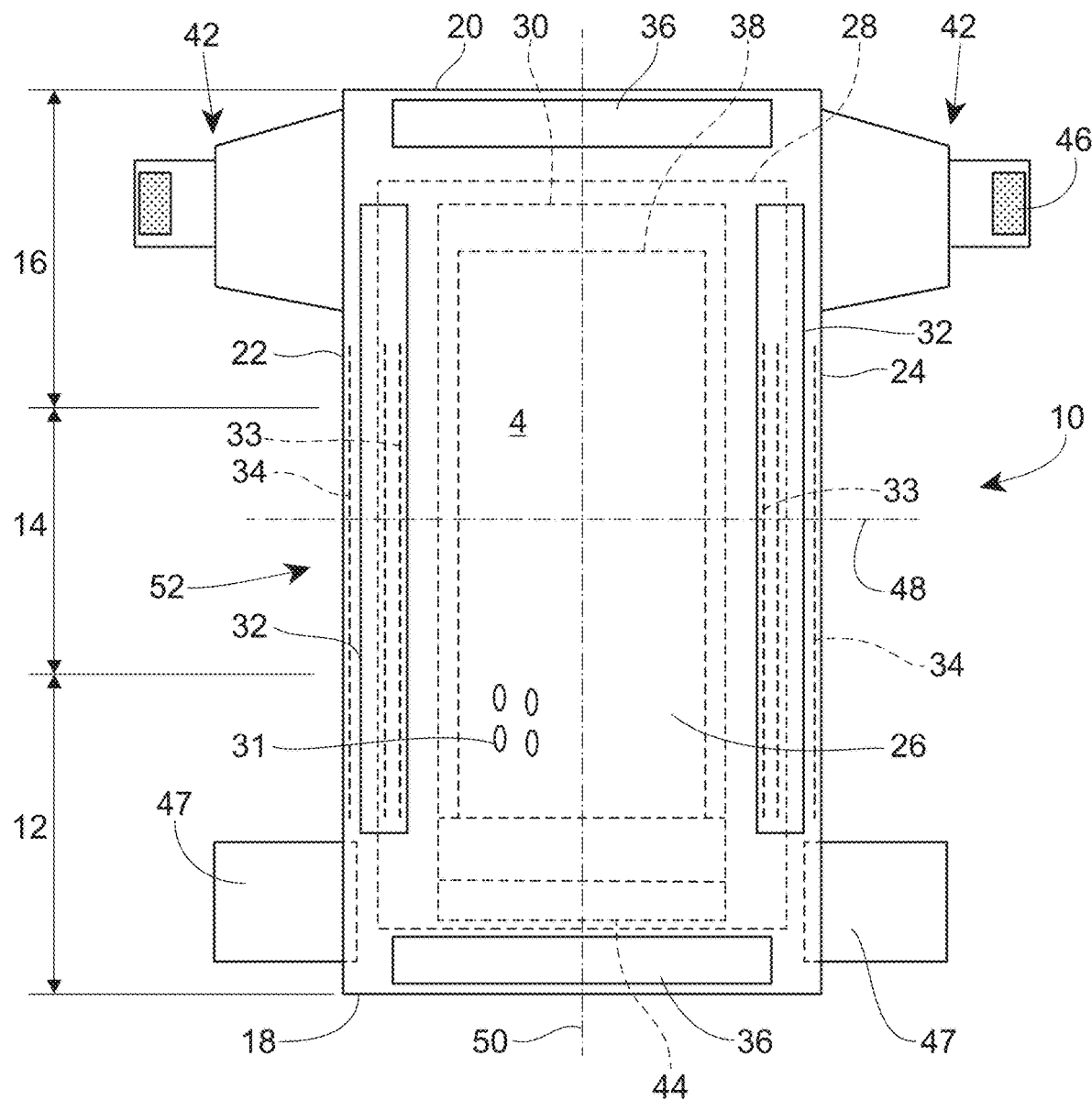
FIG. 2 is a plan view of the example absorbent article of FIG. 1, wearer-facing surface facing the viewer, in a flat laid-out state.
Figure 3:
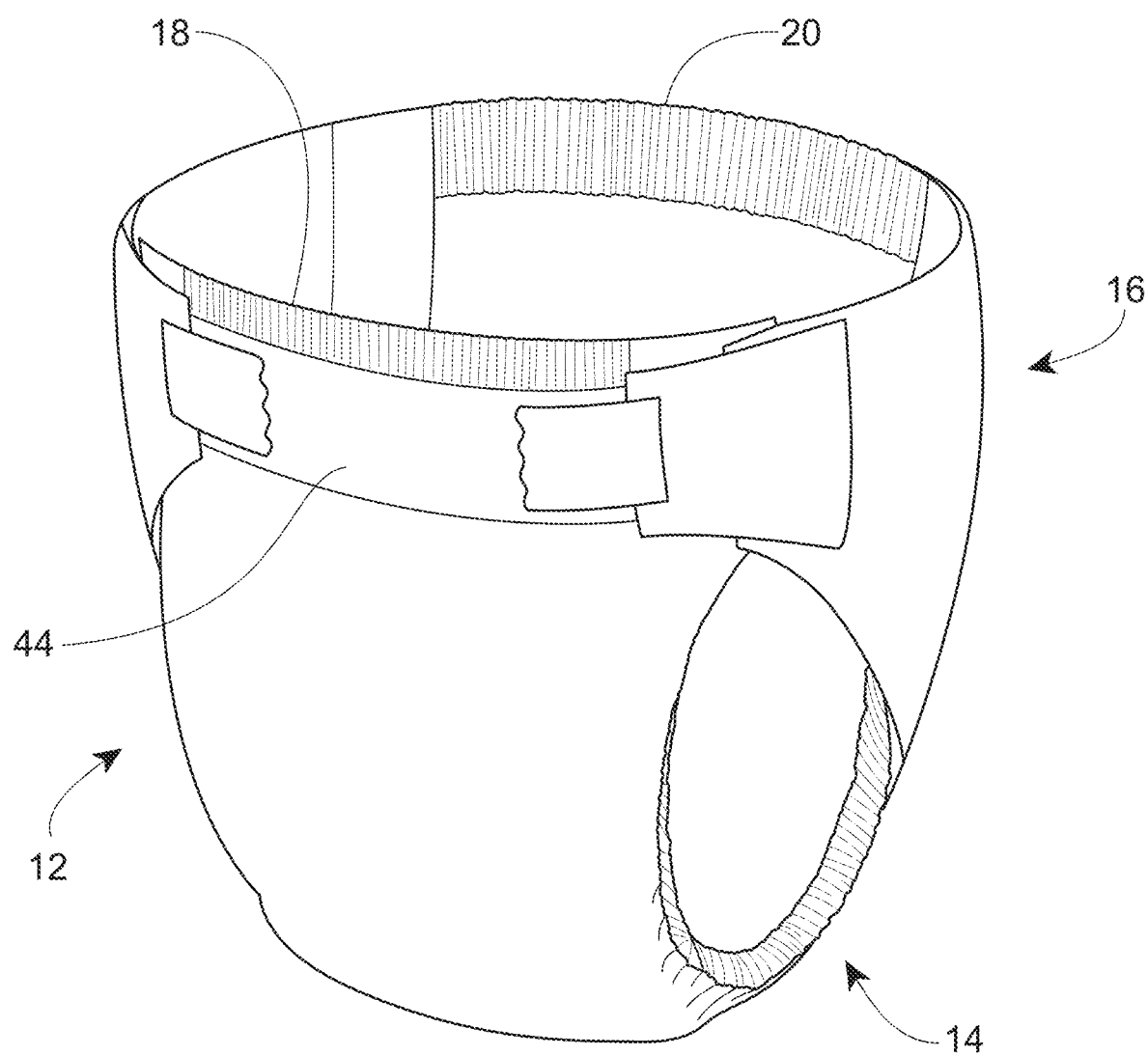
FIG. 3 is a front perspective view of the absorbent article of FIGS. 1 and 2 in a fastened configuration.

An absorbent article may comprise the nonwoven apertured webs or topsheets of the present disclosure. An example absorbent article 10, shown in the form of a taped diaper, is represented in FIGS. 1, 2, and 3. FIG. 1 is a plan view of the example absorbent article 10, garment-facing surface 2 facing the viewer in a flat, laid-out state (i.e., no elastic contraction). FIG. 2 is a plan view of the example absorbent article 10 of FIG. 1, wearer-facing surface 4 facing the viewer in a flat, laid-out state. FIG. 3 is a front perspective view of the absorbent article 10 of FIGS. 1 and 2 in a fastened configuration. The absorbent articles 10 of FIGS. 1-3 is shown for illustration purposes only as the present disclosure may be used for making a wide variety of diapers, including adult incontinence products, pants, or other absorbent articles, such as sanitary napkins and absorbent pads, for example.

Referring to FIG. 1, the absorbent article 10 may comprise a front waist region 12, a crotch region 14, and a back waist region 16. The crotch region 14 may extend intermediate the front waist region 12 and the back waist region 16. The front wait region 12, the crotch region 14, and the back waist region 16 may each be about ⅓ of the length of the absorbent article 10. The absorbent article 10 may comprise a front end edge 18, a back end edge 20 opposite to the front end edge 18, and longitudinally extending, transversely opposed side edges 22 and 24 defined by the chassis 52.

The absorbent article 10 may comprise a liquid permeable topsheet 26, a liquid impermeable backsheet 28, and an absorbent core 30 positioned at least partially intermediate the topsheet 26 and the backsheet 28. The absorbent article 10 may also comprise one or more pairs of barrier leg cuffs 32 with or without elastics 33, one or more pairs of leg elastics 34, one or more elastic waistbands 36, and/or one or more acquisition materials 38. The acquisition material or materials 38 may be positioned intermediate the topsheet 26 and the absorbent core 30. An outer cover nonwoven material 40, such as a nonwoven material, may cover a garment-facing side of the backsheet 28. The absorbent article 10 may comprise back ears 42 in the back waist region 16. The back ears 42 may comprise fasteners 46 and may extend from the back waist region 16 of the absorbent article 10 and attach (using the fasteners 46) to the landing zone area or landing zone material 44 on a garment-facing portion of the front waist region 12 of the absorbent article 10. The absorbent article 10 may also have front ears 47 in the front waist region 12. The absorbent article 10 may have a central lateral (or transverse) axis 48 and a central longitudinal axis 50. The central lateral axis 48 extends perpendicular to the central longitudinal axis 50.

Figure 4:
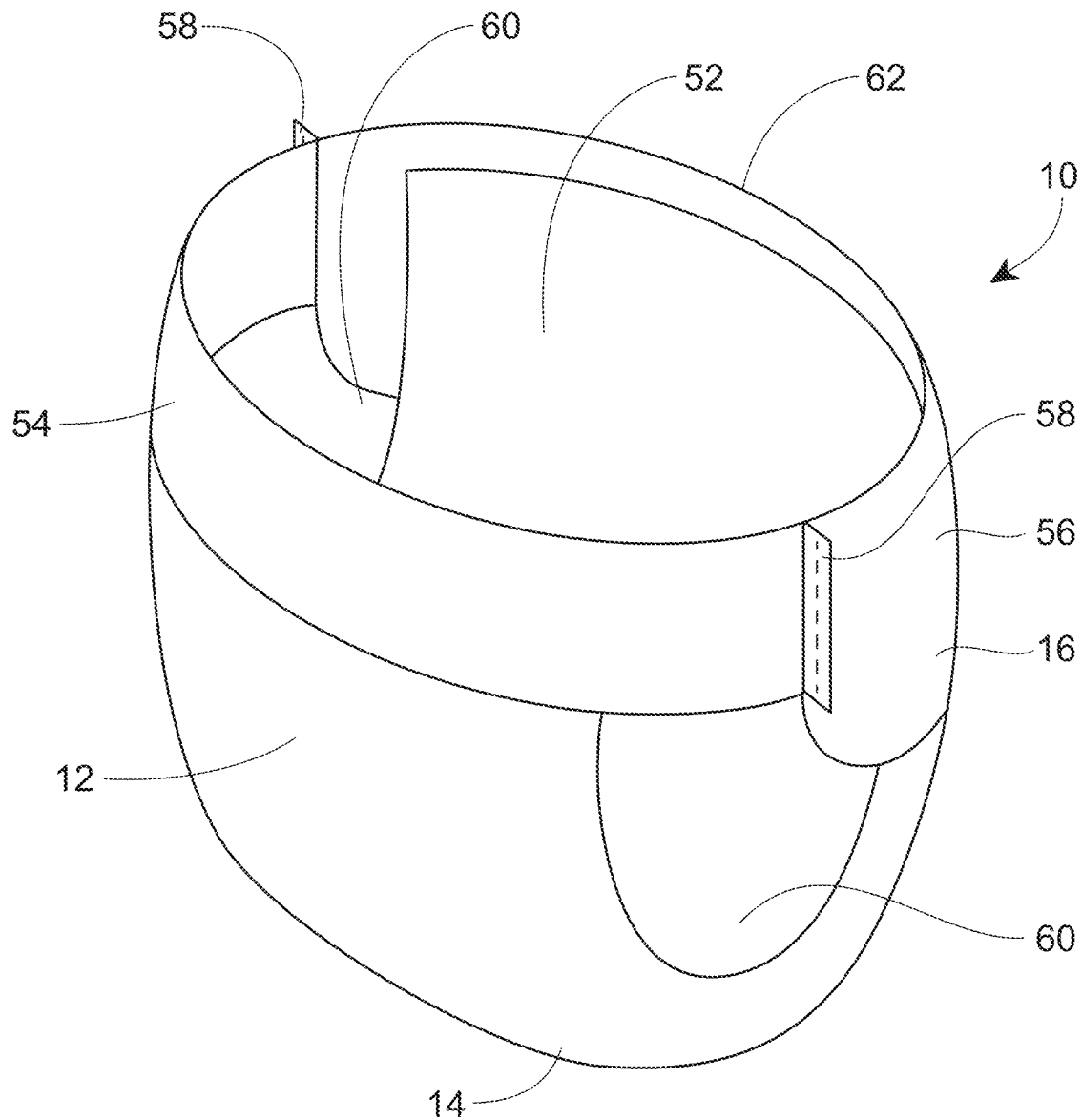
FIG. 4 is a front perspective view of an absorbent article in the form of a pant.
Figure 5:
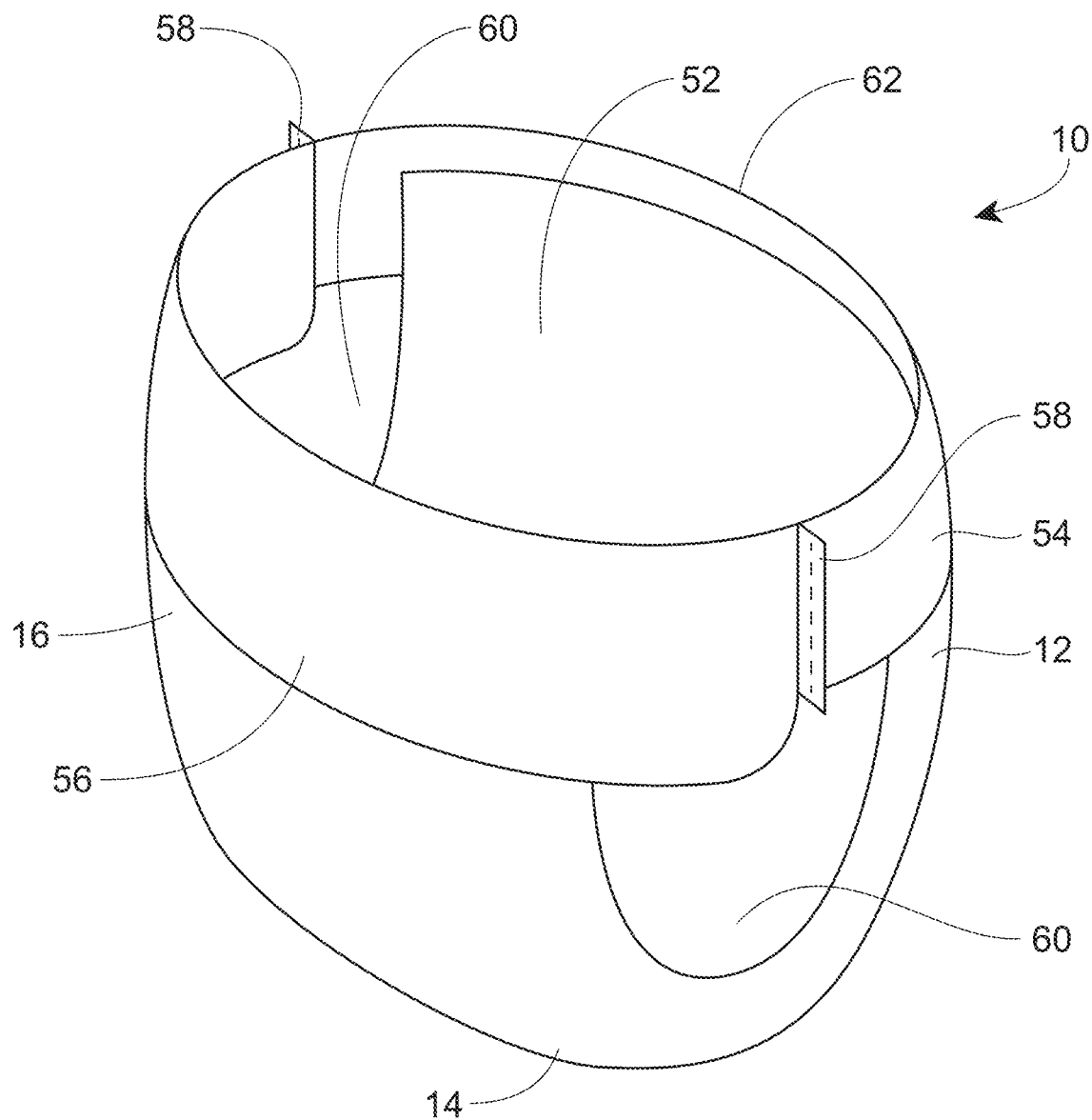
FIG. 5 is a rear perspective view of the absorbent article of FIG. 4.
Figure 6:
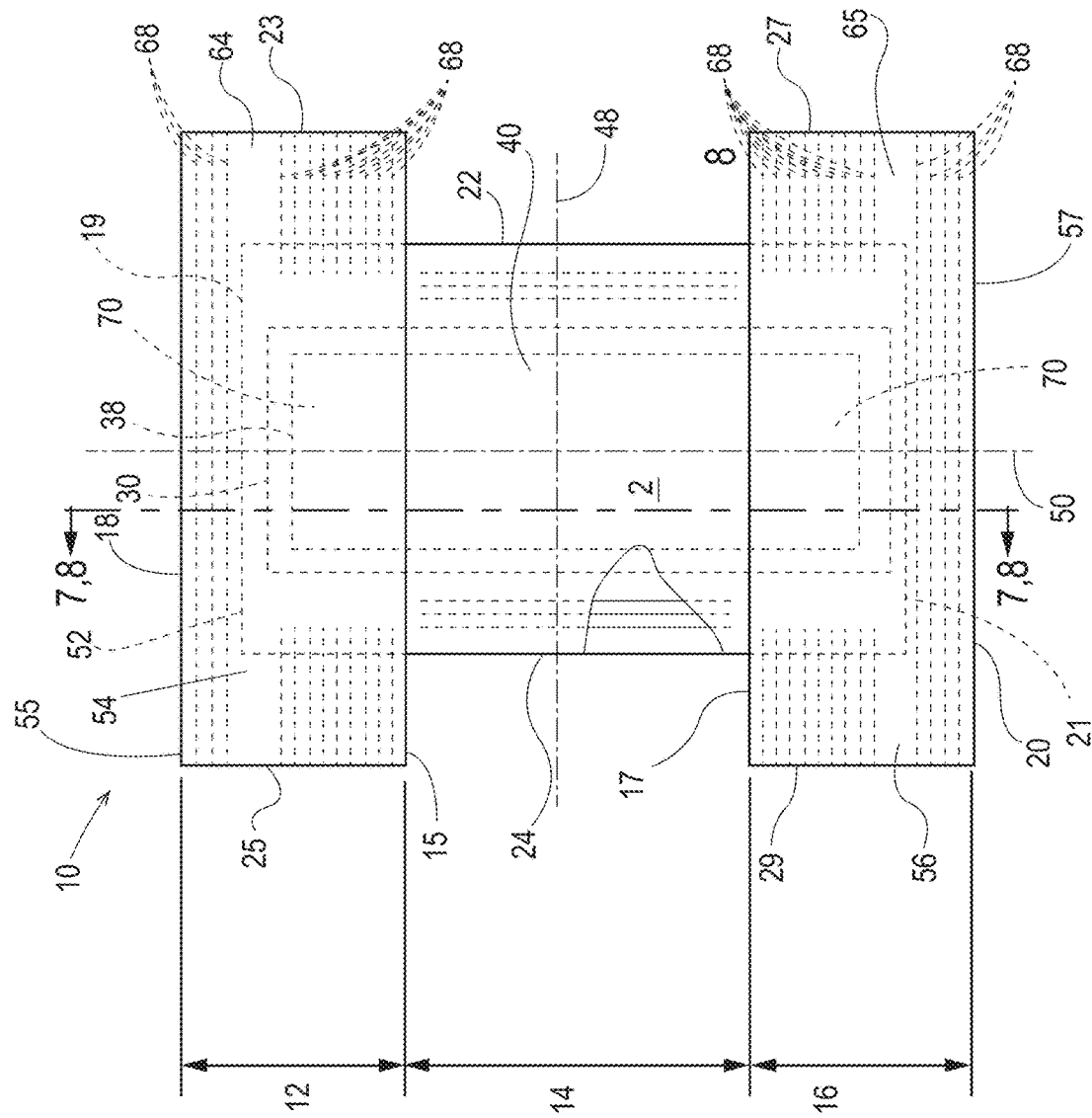
FIG. 6 is a plan view of the absorbent article of FIG. 4, laid flat, with a garment-facing surface facing the viewer.
Figure 7:
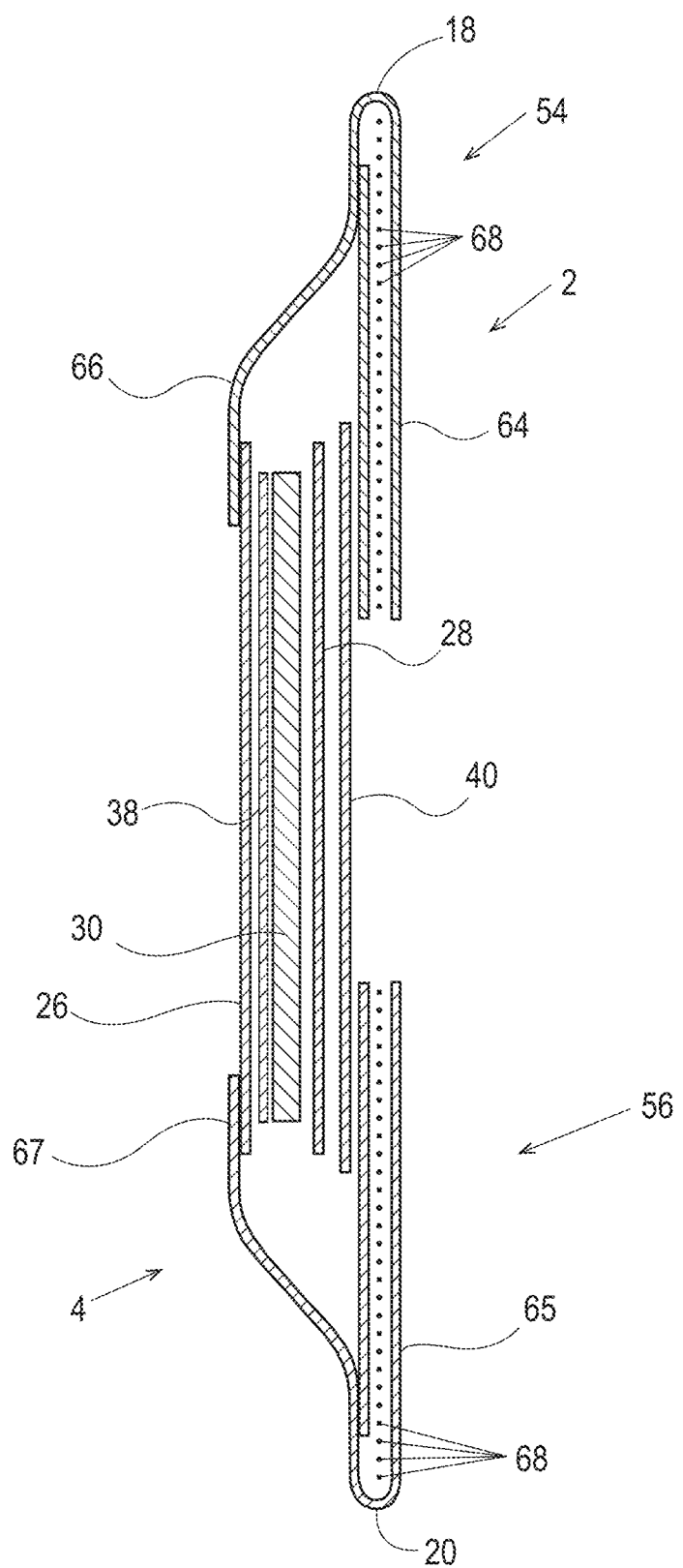
FIG. 7 is a cross-sectional view of the absorbent article of FIG. 6 taken about line 7-7 of FIG. 6.
Figure 8:
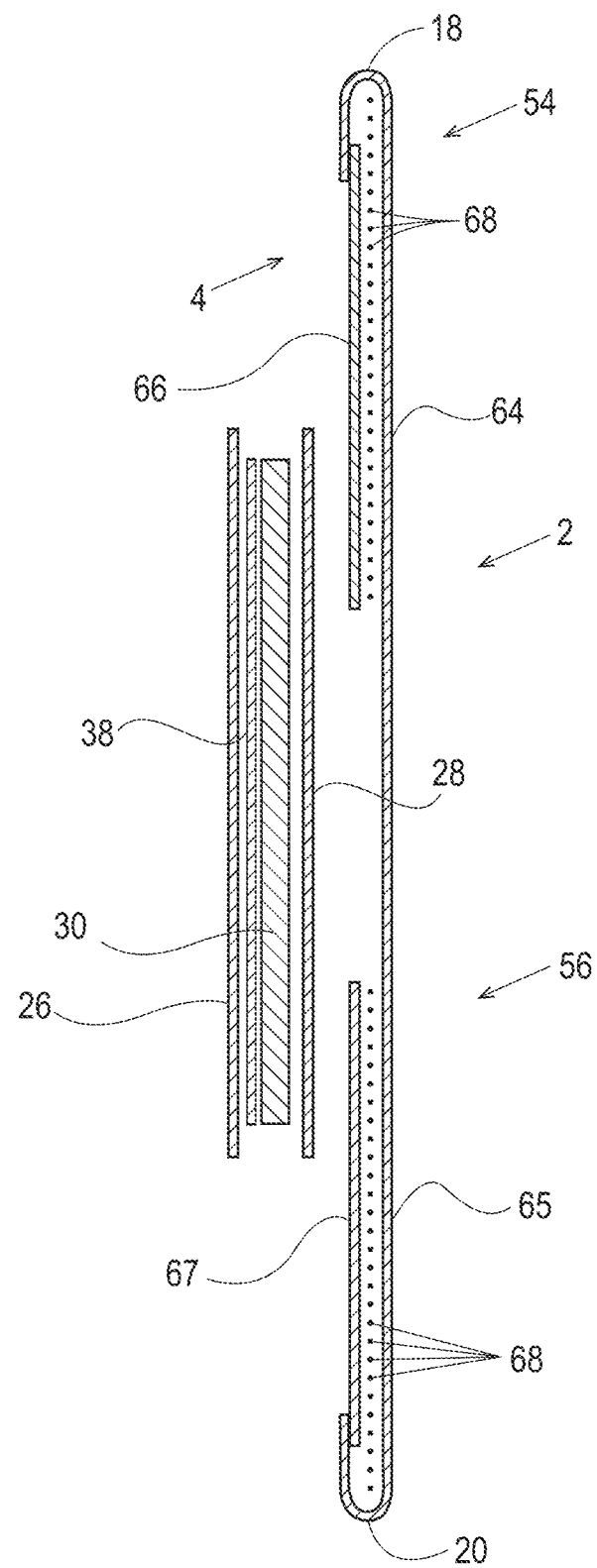
FIG. 8 is a cross-sectional view of the absorbent article of FIG. 6 taken about line 8-8 of FIG. 6.

In other instances, the absorbent article may be in the form of a pant having permanent or refastenable side seams. Suitable refastenable seams are disclosed in U.S. Pat. Appl. Pub. No. 2014/0005020 and U.S. Pat. No. 9,421,137. Referring to FIGS. 4-8, an example absorbent article 10 in the form of a pant is illustrated. FIG. 4 is a front perspective view of the absorbent article 10. FIG. 5 is a rear perspective view of the absorbent article 10. FIG. 6 is a plan view of the absorbent article 10, laid flat, with the garment-facing surface facing the viewer. Elements of FIG. 4-8 having the same reference number as described above with respect to FIGS. 1-3 may be the same element (e.g., absorbent core 30). FIG. 7 is an example cross-sectional view of the absorbent article taken about line 7-7 of FIG. 6. FIG. 8 is an example cross-sectional view of the absorbent article taken about line 8-8 of FIG. 6. FIGS. 7 and 8 illustrate example forms of front and back belts 54, 56. The absorbent article 10 may have a front waist region 12, a crotch region 14, and a back waist region 16. Each of the regions 12, 14, and 16 may be ⅓ of the length of the absorbent article 10. The absorbent article 10 may have a chassis 52 (sometimes referred to as a central chassis or central panel) comprising a topsheet 26, a backsheet 28, and an absorbent core 30 disposed at least partially intermediate the topsheet 26 and the backsheet 28, and an optional acquisition material 38, similar to that as described above with respect to FIGS. 1-3. The absorbent article 10 may comprise a front belt 54 in the front waist region 12 and a back belt 56 in the back waist region 16. The chassis 52 may be joined to a wearer-facing surface 4 of the front and back belts 54, 56 or to a garment-facing surface 2 of the belts 54, 56. Side edges 23 and 25 of the front belt 54 may be joined to side edges 27 and 29, respectively, of the back belt 56 to form two side seams 58. The side seams 58 may be any suitable seams known to those of skill in the art, such as butt seams or overlap seams, for example. When the side seams 58 are permanently formed or refastenably closed, the absorbent article 10 in the form of a pant has two leg openings 60 and a waist opening circumference 62. The side seams 58 may be permanently joined using adhesives or bonds, for example, or may be refastenably closed using hook and loop fasteners, for example.

Belts

Referring to FIGS. 7 and 8, the front and back belts 54 and 56 may comprise front and back inner belt layers 66 and 67 and front and back outer belt layers 64 and 65 having an elastomeric material (e.g., strands 68 or a film (which may be apertured)) disposed at least partially therebetween. The elastic elements 68 or the film may be relaxed (including being cut) to reduce elastic strain over the absorbent core 30 or, may alternatively, run continuously across the absorbent core 30. The elastics elements 68 may have uniform or variable spacing therebetween in any portion of the belts. The elastic elements 68 may also be pre-strained the same amount or different amounts. The front and/or back belts 54 and 56 may have one or more elastic element free zones 70 where the chassis 52 overlaps the belts 54, 56. In other instances, at least some of the elastic elements 68 may extend continuously across the chassis 52.

The front and back inner belt layers 66, 67 and the front and back outer belt layers 64, 65 may be joined using adhesives, heat bonds, pressure bonds or thermoplastic bonds. Various suitable belt layer configurations can be found in U.S. Pat. Appl. Pub. No. 2013/0211363.

Front and back belt end edges 55 and 57 may extend longitudinally beyond the front and back chassis end edges 19 and 21 (as shown in FIG. 6) or they may be co-terminus. The front and back belt side edges 23, 25, 27, and 29 may extend laterally beyond the chassis side edges 22 and 24. The front and back belts 54 and 56 may be continuous (i.e., having at least one layer that is continuous) from belt side edge to belt side edge (e.g., the transverse distances from 23 to 25 and from 27 to 29). Alternatively, the front and back belts 54 and 56 may be discontinuous from belt side edge to belt side edge (e.g., the transverse distances from 23 to 25 and 27 to 29), such that they are discrete.

As disclosed in U.S. Pat. No. 7,901,393, the longitudinal length (along the central longitudinal axis 50) of the back belt 56 may be greater than the longitudinal length of the front belt 54, and this may be particularly useful for increased buttocks coverage when the back belt 56 has a greater longitudinal length versus the front belt 54 adjacent to or immediately adjacent to the side seams 58.

The front outer belt layer 64 and the back outer belt layer 65 may be separated from each other, such that the layers are discrete or, alternatively, these layers may be continuous, such that a layer runs continuously from the front belt end edge 55 to the back belt end edge 57. This may also be true for the front and back inner belt layers 66 and 67—that is, they may also be longitudinally discrete or continuous. Further, the front and back outer belt layers 64 and 65 may be longitudinally continuous while the front and back inner belt layers 66 and 67 are longitudinally discrete, such that a gap is formed between them—a gap between the front and back inner and outer belt layers 64, 65, 66, and 67 is shown in FIG. 7 and a gap between the front and back inner belt layers 66 and 67 is shown in FIG. 8.

The front and back belts 54 and 56 may include slits, holes, apertures, and/or perforations providing increased breathability, softness, and a garment-like texture. Underwear-like appearance can be enhanced by substantially aligning the waist and leg edges at the side seams 58 (see FIGS. 4 and 5).

The front and back belts 54 and 56 may comprise graphics (see e.g., 78 of FIG. 1). The graphics may extend substantially around the entire circumference of the absorbent article 10 and may be disposed across side seams 58 and/or across proximal front and back belt seams 15 and 17; or, alternatively, adjacent to the seams 58, 15, and 17 in the manner described in U.S. Pat. No. 9,498,389 to create a more underwear-like article. The graphics may also be discontinuous.

Alternatively, instead of attaching belts 54 and 56 to the chassis 52 to form a pant, discrete side panels may be attached to side edges of the chassis 22 and 24. Suitable forms of pants comprising discrete side panels are disclosed in U.S. Pat. Nos. 6,645,190; 8,747,379; 8,372,052; 8,361,048; 6,761,711; 6,817,994; 8,007,485; 7,862,550; 6,969,377; 7,497,851; 6,849,067; 6,893,426; 6,953,452; 6,840,928; 8,579,876; 7,682,349; 7,156,833; and 7,201,744.

The apertured nonwoven webs of the present disclosure may be used as portions of the belts in an absorbent article.

Topsheet

Referring again to FIG. 2, the topsheet 26 is the part of the absorbent article 10 that is in contact with the wearer's skin. The topsheet 26 may be joined to portions of the backsheet 28, the absorbent core 30, the barrier leg cuffs 32, and/or any other layers as is known to those of ordinary skill in the art. The topsheet 26 may be compliant, soft-feeling, and non-irritating to the wearer's skin. The topsheet 26 may have a first side and a second side. The topsheet may have one or more layers. Where the topsheet comprises a first layer and a second layer joined to the first layer, for example a laminate topsheet. The first layer may be disposed on the first side of the topsheet 26, and the second layer may be disposed on the second side of the topsheet 26. At least a portion of, or all of, the topsheet 26 may be permeable, permitting bodily exudates to readily penetrate through its thickness. In other instances, the topsheet may be hydrophobic and impermeable, but define apertures to allow for bodily exudate penetration.

A suitable topsheet 26 may be manufactured from one or more nonwoven webs. The nonwoven webs may comprise synthetic fibers or filaments (e.g., polyester or polypropylene or bicomponent PE/PP fibers or mixtures thereof), a combination of natural and synthetic fibers, or only natural fibers. Where the topsheet 26 has more than one layer, each layer of the topsheet 26 may all be made of the same material, or one or more layers may be made of a different material. In some instances, a first layer may comprise a carded natural fiber nonwoven web, while a second layer may comprise a synthetic continuous fiber nonwoven web. As an example, the first layer may comprise carded cotton fibers and the second layer may comprise mono-component or bi-component continuous fibers that have been air-through bonded.

Figure 2A:
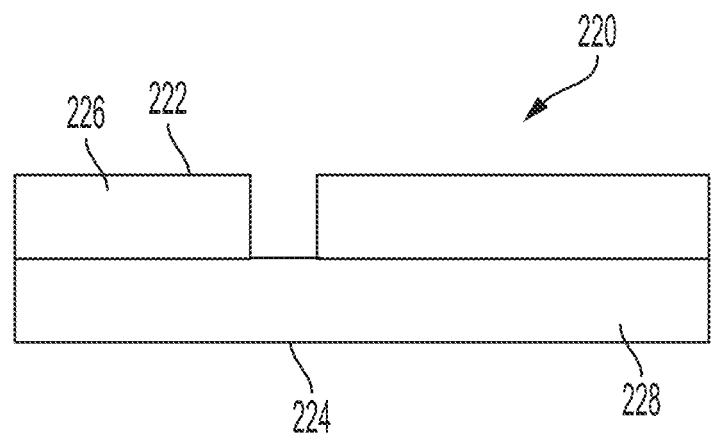
FIG. 2A is schematic illustration of a multi-layer topsheet or nonwoven web.

FIG. 2A is schematic illustration of a multi-layer topsheet 220 or nonwoven web. Where the topsheet comprises more than one layer, the first layer 226 may form a first side 222 of the topsheet 220. The first side 222 of the topsheet 220 may be disposed to face the wearer of the absorbent article. Alternatively, the first side 222 of the topsheet 220 may be disposed to face the acquisition layer (38 of FIG. 2) or the absorbent core (30 of FIG. 2) of the absorbent article (10 of FIG. 2). Where the topsheet 220 comprises two layers, the second layer 228 of the topsheet 220 may be in face-to-face contact with the first layer 226 of the topsheet 220 and may form the second side 224 of the topsheet 220. The second side 224 of the topsheet 220 may be disposed to face the acquisition layer (38 of FIG. 2) or the absorbent core (30 of FIG. 2) of the absorbent article (10 of FIG. 2). Alternatively, the second side 224 of the topsheet 220 may be disposed to face the wearer of the absorbent article. One or more additional layers may be disposed between the first and second layers. The multiple layers of the topsheet may be placed in a face-to-face relationship and may be joined by applying welds or bonds between the multiple layers of the topsheet, or may be joined by one or more adhesives.

Referring again to FIG. 2, any portion of the topsheet 26 may be coated with a skin care composition, an antibacterial agent, a surfactant, and/or other beneficial agents. In certain instances, the topsheet 26 may be hydrophilic or hydrophobic or may have hydrophilic and/or hydrophobic portions or layers. The topsheet 26 may be naturally hydrophobic or may be chemically treated to be hydrophobic. If the topsheet 26 is hydrophobic, typically apertures 31 will be present so that bodily exudates may pass through the topsheet 26. For example, a nonwoven topsheet 26 may be naturally hydrophilic, and may be treated with a chemical treatment to cause the topsheet 26 to become hydrophobic. Where the topsheet 26 comprises only one layer, just the wearer-facing surface of the topsheet 26 may be treated to be hydrophobic. Where the topsheet 26 comprises more than one layer, just the first, wearer-facing layer or wearer-facing surface may be treated to be hydrophobic. For example, referring to FIG. 2A, a multi-layered topsheet 220 may comprise a first hydrophobic layer 226, where the first hydrophobic layer 226 is either naturally hydrophobic or treated to be hydrophobic, and a second hydrophilic layer 228. In other instances, only the first surface 222 of the first layer 226 may be treated to be hydrophobic with the remainder of the layer 226 being hydrophilic. Such a multi-layered topsheet 220 may provide improved bodily exudate handling by directing bodily exudates away from the first hydrophobic layer 226 and toward the second hydrophilic layer 228, which is proximate to an acquisition material or an absorbent core material. In other instances, more than one or all of the layers of the topsheet 220 may be hydrophobic. In still other instances, only portions of the one or more layers may be hydrophobic or hydrophilic.

Backsheet

The backsheet 28 is generally that portion of the absorbent article 10 positioned proximate to the garment-facing surface of the absorbent core 30. The backsheet 28 may be joined to portions of the topsheet 26, the outer cover nonwoven material 40, the absorbent core 30, and/or any other layers of the absorbent article by any attachment methods known to those of skill in the art. The backsheet 28 prevents, or at least inhibits, the bodily exudates absorbed and contained in the absorbent core 10 from soiling articles such as bedsheets, undergarments, and/or clothing. The backsheet is typically liquid impermeable, or at least substantially liquid impermeable. The backsheet may, for example, be or comprise a thin plastic film, such as a thermoplastic film having a thickness of about 0.012 mm to about 0.051 mm. Other suitable backsheet materials may include breathable materials which permit vapors to escape from the absorbent article, while still preventing, or at least inhibiting, bodily exudates from passing through the backsheet.

Outer Cover Nonwoven Material

The outer cover nonwoven material (sometimes referred to as a backsheet nonwoven) 40 may comprise one or more nonwoven materials joined to the backsheet 28 and that covers the backsheet 28. The outer cover nonwoven material 40 forms at least a portion of the garment-facing surface 2 of the absorbent article 10 and effectively "covers" the backsheet 28 so that film is not present on the garment-facing surface 2. The outer cover nonwoven material 40 may comprise a bond pattern, apertures, and/or three-dimensional features. The apertured nonwoven webs of the present disclosure may form portions of, or all of, the outer cover nonwoven material 40.

Absorbent Core

Figure 9:
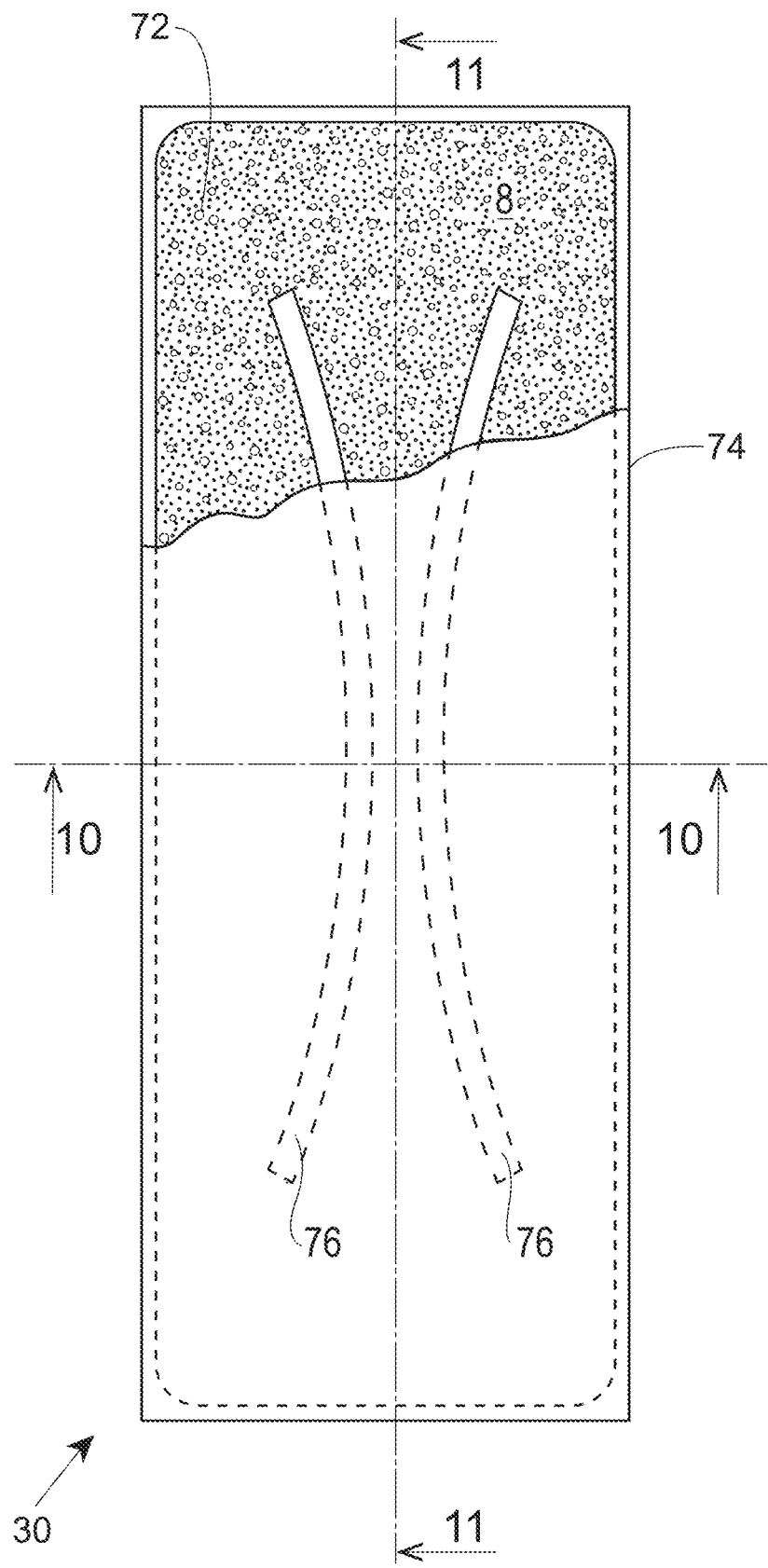
FIG. 9 is a plan view of an example absorbent core for an absorbent article.

As used herein, the term "absorbent core" 30 refers to the component of the absorbent article 10 having the most absorbent capacity and that comprises an absorbent material. Referring to FIGS. 9-11, in some instances, absorbent material 72 may be positioned within a core bag or a core wrap 74. The absorbent material may be profiled or not profiled, depending on the specific absorbent article. The absorbent core 30 may comprise, consist essentially of, or consist of, a core wrap, absorbent material 72, and glue enclosed within the core wrap. The absorbent material may comprise superabsorbent polymers, a mixture of superabsorbent polymers and air felt, only air felt, and/or a high internal phase emulsion foam. In some instances, the absorbent material may comprise at least 80%, at least 85%, at least 90%, at least 95%, at least 99%, or up to 100% superabsorbent polymers, by weight of the absorbent material. In such instances, the absorbent material may be free of air felt, or at least mostly free of air felt. The absorbent core periphery, which may be the periphery of the core wrap, may define any suitable shape, such as rectangular "T," "Y," "hour-glass," or "dog-bone" shaped, for example. An absorbent core periphery having a generally "dog bone" or "hour-glass" shape may taper along its width towards the crotch region 14 of the absorbent article 10.

Referring to FIGS. 9-11, the absorbent core 30 may have areas having little or no absorbent material 72, where a wearer-facing surface of the core bag 74 may be joined to a garment-facing surface of the core bag 74. These areas having little or no absorbent material and may be referred to as "channels" 76. These channels can embody any suitable shapes and any suitable number of channels may be provided. In other instances, the absorbent core may be embossed to create the impression of channels. The absorbent core in FIGS. 9-11 is merely an example absorbent core. Many other absorbent cores with or without channels are also within the scope of the present disclosure.

Barrier Leg Cuffs/Leg Elastics

Referring to FIGS. 1 and 2, for example, the absorbent article 10 may comprise one or more pairs of barrier leg cuffs 32 and one or more pairs of leg elastics 34. The barrier leg cuffs 32 may be positioned laterally inboard of leg elastics 34. Each barrier leg cuff 32 may be formed by a piece of material which is bonded to the absorbent article 10 so it can extend upwards from a wearer-facing surface 4 of the absorbent article 10 and provide improved containment of body exudates approximately at the junction of the torso and legs of the wearer. The barrier leg cuffs 32 are delimited by a proximal edge joined directly or indirectly to the topsheet and/or the backsheet and a free terminal edge, which is intended to contact and form a seal with the wearer's skin. The barrier leg cuffs 32 may extend at least partially between the front end edge 18 and the back end edge 20 of the absorbent article 10 on opposite sides of the central longitudinal axis 50 and may be at least present in the crotch region 14. The barrier leg cuffs 32 may each comprise one or more elastics 33 (e.g., elastic strands or strips) near or at the free terminal edge. These elastics 33 cause the barrier leg cuffs 32 to help form a seal around the legs and torso of a wearer. The leg elastics 34 extend at least partially between the front end edge 18 and the back end edge 20. The leg elastics 34 essentially cause portions of the absorbent article 10 proximate to the chassis side edges 22, 24 to help form a seal around the legs of the wearer. The leg elastics 34 may extend at least within the crotch region 14.

Elastic Waistband

Referring to FIGS. 1 and 2, the absorbent article 10 may comprise one or more elastic waistbands 36. The elastic waistbands 36 may be positioned on the garment-facing surface 2 or the wearer-facing surface 4. As an example, a first elastic waistband 36 may be present in the front waist region 12 near the front belt end edge 18 and a second elastic waistband 36 may be present in the back waist region 16 near the back end edge 20. The elastic waistbands 36 may aid in sealing the absorbent article 10 around a waist of a wearer and at least inhibiting bodily exudates from escaping the absorbent article 10 through the waist opening circumference. In some instances, an elastic waistband may fully surround the waist opening circumference of an absorbent article.

Acquisition Materials

Referring generally to FIGS. 1, 2, 7, and 8, one or more acquisition materials or acquisition layers 38 may be present at least partially intermediate the topsheet 26 and the absorbent core 30. The acquisition materials 38 may be hydrophilic materials that provide significant wicking of bodily exudates. These materials may dewater the topsheet 26 and quickly move bodily exudates into the absorbent core 30. The acquisition materials 38 may comprise one or more nonwoven materials, foams, cellulosic materials, cross-linked cellulosic materials, air laid cellulosic nonwoven materials, spunlace materials, or combinations thereof, for example. In some instances, portions (or fibers) of the acquisition materials 38 may extend through portions of the topsheet 26, portions of the topsheet 26 may extend through portions of the acquisition materials 38, and/or the topsheet 26 may be nested with the acquisition materials 38. As an example, portions (or fibers) of the acquisition materials 38 may extend through the plurality of apertures 31 in the topsheet 26. Extension of the acquisition materials through the apertures 31 may impart the benefit of wicking bodily exudates from the hydrophobic (or partially hydrophobic) topsheet 26 into the acquisition layer 38 and further into the absorbent core 30.

An acquisition material 38 may have a width and/or a length that are smaller than the width and length of the topsheet 26. The acquisition material may be a secondary topsheet in the sanitary napkin or liner context. The acquisition material may have one or more channels as described above with reference to the absorbent core 30 (including the embossed version). The channels in the acquisition material may align or not align with channels in the absorbent core 30. In an example, a first acquisition material may comprise a nonwoven material and a second acquisition material may comprise a cross-linked cellulosic material.

The acquisition material 38 may be or may comprise a nonwoven material, for example a SMS or SMMS material, comprising a spunbonded, a melt-blown and a further spunbonded layer or alternatively a carded chemical-bonded nonwoven. The acquisition materials may be non-apertured or apertured. "Non-apertured" in the context of the acquisition material means that the acquisition material does not have openings additionally formed in the acquisition material after the material that comprises the acquisition material has been made (i.e., by an aperturing process, such as pin aperturing). For example, an acquisition material may comprise pores, which are voids in a nonwoven web that are a result of the manner in which the fibers of the web were laid down and bonded. Since pores are a result of the formation of the material that comprises the acquisition material and not created after the material has been made, they are not apertures for the purposes of this disclosure. Therefore, an acquisition material that comprises pores may be considered non-apertured for purposes of this disclosure.

The acquisition material may be latex bonded. Carded, resin-bonded nonwovens may be used as an acquisition material, in particular where the fibers used are solid round or round and hollow PET staple fibers (such as a 50/50 or 40/60 mix of 6 denier and 9 denier fibers). The acquisition materials 38 may be stabilized by a latex binder, for example a styrene-butadiene latex binder (SB latex). Processes for obtaining such latexes are known, for example, from EP 149 880 (Kwok) and U.S. Pat. Appl. Pub. No. 2003/0105190 (Diehl et al.). The binder may be present in the acquisition materials 38 in excess of 12%, 14% or 16% by weight, but may be present by not more than 30%, or not more than 25% by weight of the acquisition materials. SB latex is available under the trade name GENFLO™ 3160 (OMNOVA Solutions Inc.; Akron, Ohio).

The acquisition material 38 may form a laminate with the topsheet 26. The topsheet 26 and the acquisition material 38 may be placed in a face-to-face relationship and may be joined by applying welds or bonds between the topsheet 26 and the acquisition material 38 or may be joined by one or more adhesives.

Landing Zone

Referring to FIGS. 1 and 2, the absorbent article 10 may have a landing zone area 44 that is formed on a portion of the garment-facing surface 2 of the outer cover nonwoven material 40. The landing zone area 44 may be in the back waist region 16 if the absorbent article 10 fastens from front to back or may be in the front waist region 12 if the absorbent article 10 fastens back to front. In some instances, the landing zone 44 may be or may comprise one or more discrete nonwoven materials that are attached to a portion of the outer cover nonwoven material 40 in the front waist region 12 or the back waist region 16 depending upon whether the absorbent article fastens in the front or the back. In essence, the landing zone 44 is configured to receive the fasteners 46 and may comprise, for example, a plurality of loops configured to be engaged with, a plurality of hooks on the fasteners 46, or vice versa. In other instances, a landing zone may not be provided and the outer cover nonwoven material 40 may function as a landing zone. The landing zone may be formed of the apertured nonwoven webs of the present disclosure.

Wetness Indicator/Graphics

Referring to FIG. 1, the absorbent articles 10 of the present disclosure may comprise graphics 78 and/or wetness indicators 80 that are visible from the garment-facing surface 2. The graphics 78 may be printed on the landing zone 40, the backsheet 28, and/or at other locations. The wetness indicators 80 are typically applied to the absorbent core facing side of the backsheet 28, so that they can be contacted by bodily exudates within the absorbent core 30. In some instances, the wetness indicators 80 may form portions of the graphics 78. For example, a wetness indicator may appear or disappear and create/remove a character within some graphics. In other instances, the wetness indicators 80 may coordinate (e.g., same design, same pattern, same color) or not coordinate with the graphics 78.

Front and Back Ears

Referring to FIGS. 1 and 2, as referenced above, the absorbent article 10 may have front and/or back ears 47, 42 in a taped diaper context. Only one set of ears may be required in most taped diapers. The single set of ears may comprise fasteners 46 configured to engage the landing zone or landing zone area 44. If two sets of ears are provided, in most instances, only one set of the ears may have fasteners 46, with the other set being free of fasteners. The ears, or portions thereof, may be elastic or may have elastic panels. In an example, an elastic film or elastic strands may be positioned intermediate a first nonwoven material and a second nonwoven material. The elastic film may or may not be apertured. The ears may be shaped. The ears may be integral (e.g., extension of the outer cover nonwoven material 40, the backsheet 28, and/or the topsheet 26) or may be discrete components attached to a chassis 52 of the absorbent article on a wearer-facing surface 4, on the garment-facing surface 2, or intermediate the two surfaces 4, 2. Nonwoven portions of the front and back ears may be formed of the apertured nonwoven webs of the present disclosure.

Sensors

Referring again to FIG. 1, the absorbent articles of the present disclosure may comprise a sensor system 82 for monitoring changes within the absorbent article 10. The sensor system 82 may be discrete from or integral with the absorbent article 10. The absorbent article 10 may comprise sensors that can sense various aspects of the absorbent article 10 associated with insults of bodily exudates such as urine and/or BM (e.g., the sensor system 82 may sense variations in temperature, humidity, presence of ammonia or urea, various vapor components of the exudates (urine and feces), changes in moisture vapor transmission through the absorbent articles garment-facing layer, changes in translucence of the garment-facing layer, and/or color changes through the garment-facing layer). Additionally, the sensor system 82 may sense components of urine, such as ammonia or urea and/or byproducts resulting from reactions of these components with the absorbent article 10. The sensor system 82 may sense byproducts that are produced when urine mixes with other components of the absorbent article 10 (e.g., adhesives, superabsorbent polymer). The components or byproducts being sensed may be present as vapors that may pass through the garment-facing layer. It may also be desirable to place reactants in the absorbent article that change state (e.g. color, temperature) or create a measurable byproduct when mixed with urine or BM. The sensor system 82 may also sense changes in pH, pressure, odor, the presence of gas, blood, a chemical marker or a biological marker or combinations thereof. The sensor system 82 may have a component on or proximate to the absorbent article that transmits a signal to a receiver more distal from the absorbent article, such as an iPhone, for example. The receiver may output a result to communicate to the caregiver a condition of the absorbent article 10. In other instances, a receiver may not be provided, but instead the condition of the absorbent article 10 may be visually or audibly apparent from the sensor on the absorbent article.

Sanitary Napkin

Figure 12:
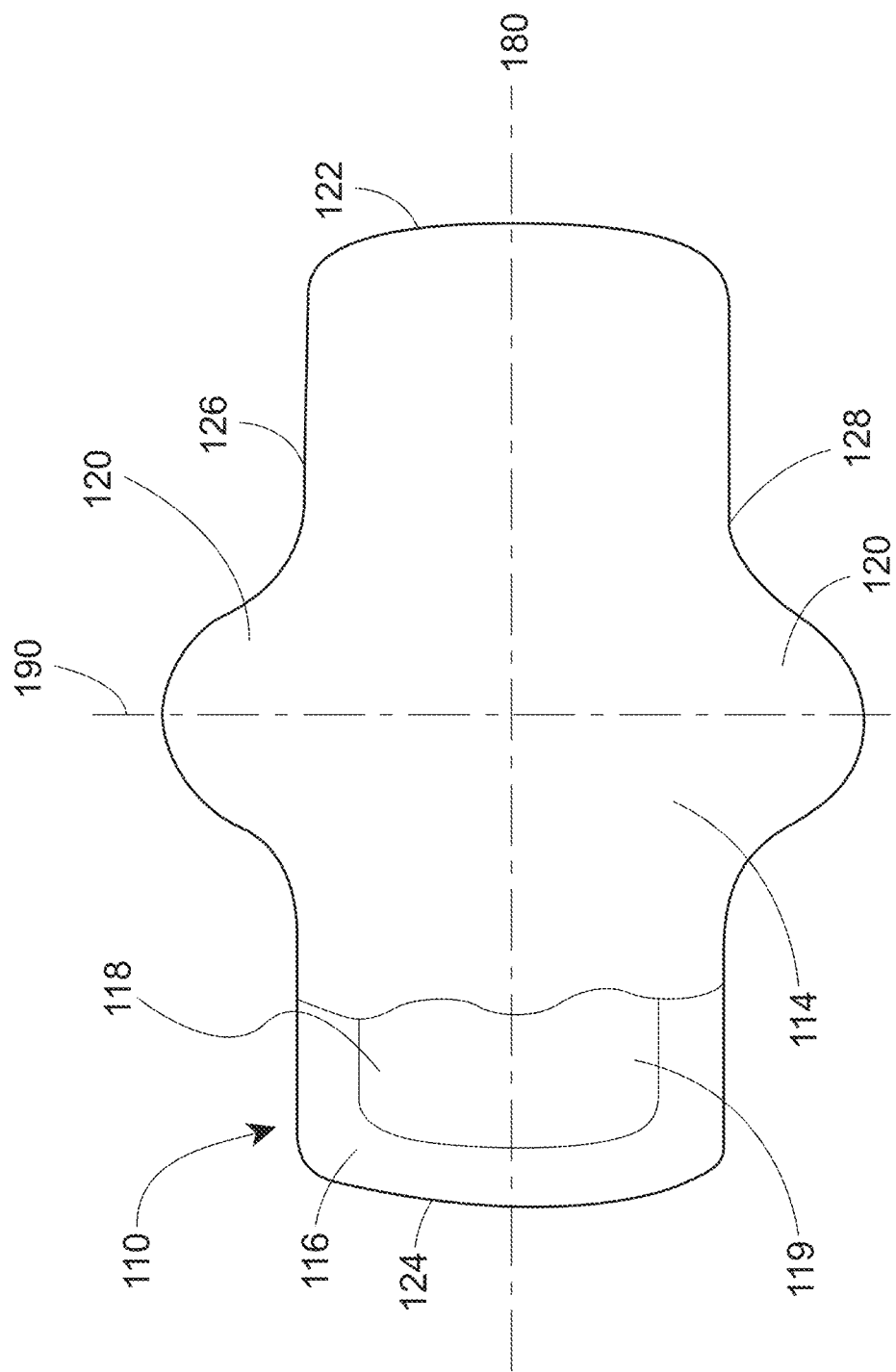
FIG. 12 is a plan view of an example absorbent article of the present disclosure that is a sanitary napkin.

Referring to FIG. 12, an absorbent article of the present disclosure may be a sanitary napkin 110. The sanitary napkin 110 may comprise a liquid permeable topsheet 114, a liquid impermeable, or substantially liquid impermeable, backsheet 116, and an absorbent core 118. The liquid impermeable backsheet 116 may or may not be vapor permeable. The absorbent core 118 may have any or all of the features described herein with respect to the absorbent core 30 and, in some forms, may have a secondary topsheet 119 (STS) instead of the acquisition materials disclosed above. The STS 119 may comprise one or more channels, as described above (including the embossed version). In some forms, channels in the STS 119 may be aligned with channels in the absorbent core 118. The sanitary napkin 110 may also comprise wings 120 extending outwardly with respect to a longitudinal axis 180 of the sanitary napkin 110. The sanitary napkin 110 may also comprise a lateral axis 190. The wings 120 may be joined to the topsheet 114, the backsheet 116, and/or the absorbent core 118. The sanitary napkin 110 may also comprise a front edge 122, a back edge 124 longitudinally opposing the front edge 122, a first side edge 126, and a second side edge 128 longitudinally opposing the first side edge 126. The longitudinal axis 180 may extend from a midpoint of the front edge 122 to a midpoint of the back edge 124. The lateral axis 190 may extend from a midpoint of the first side edge 128 to a midpoint of the second side edge 128. The sanitary napkin 110 may also be provided with additional features commonly found in sanitary napkins as is known in the art. Nonwoven components of the sanitary napkin may be formed of the apertured nonwoven webs of the present disclosure, such as the topsheet, the secondary topsheet, and/or the wings, for example.

Reversible and Configurable Absorbent Articles

Figure 13:
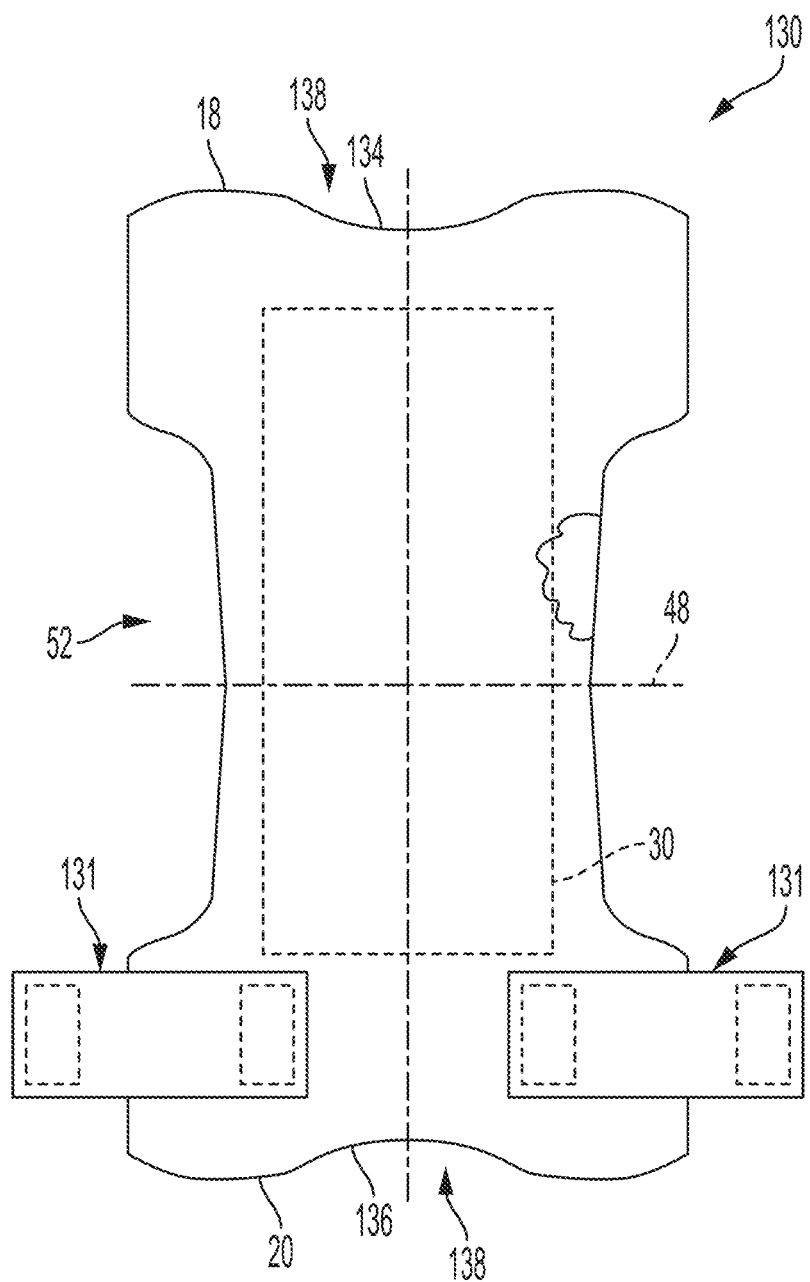
FIG. 13 is a plan view of an example absorbent article of the present disclosure for use in diapering premature or small babies or other wearers, wearer-facing surface facing the viewer, in a flat laid-out state.

Referring to FIG. 13, an absorbent article of the present disclosure may be a reversible and configurable absorbent article 130. Such an absorbent article may be suitable for premature infants, smaller babies, or other wearers. Elements of FIG. 13 having the same reference number as described above with respect to FIGS. 1-3 are the same element (e.g., absorbent core 30). The reversible and configurable absorbent article 130 may comprise a front end edge 18 and a back end edge 20. The front end edge 18 may comprise one or more first curvilinear portions 134. The back end edge 20 may comprise one or more second curvilinear portions 136. The first curvilinear portion 134 of the front end edge 18 may comprise one or more first concave portions and one or more first convex portions with respect to the central lateral axis 48. Likewise, the second curvilinear portion 136 of the back end edge 20 may comprise one or more first concave portions and one or more first convex portions with respect to the central lateral axis 48. The concave portions of the front and back end edges 18, 20, or portions thereof, may form umbilical cord or surgical site notches or recesses 138 in the front and back end edges 18, 20. The gradual slopes into the umbilical or surgical site notches or recesses 138 may be important in a premature baby context to reduce sharp edges contacting the baby. The front end edge 18 and the back end edge 20 may be substantially symmetrical about the central lateral axis 48. By having the front and back end edges substantially symmetrical about the central lateral axis, the absorbent article 130 may be reversible, thereby allowing a caregiver or nurse the ability to apply the absorbent article with either of the front or back end edge 18, 20 on a front waist of a wearer.

Referring again to FIG. 13, the reversible and configurable absorbent article 130 may comprise one or more fully removable fastening members 131. The fully removable fastening members 131 may be discrete from the chassis 52. Since the fastening members 131 are fully removeable from the absorbent article 130, they can be fastened as desired by a nurse or caregiver. In some instances, the nurse or caregiver may remove the fastening members 131 from the chassis 52 and not use them at all if the infant is in a certain position, for example. In other instances, the nurse or caregiver may only use one of the fastening members 131 if the infant is in another certain position, for example. Suitable forms of reversible and configurable absorbent articles are disclosed in U.S. Prov. Pat. Appl. No. 62/683,130, filed on Jun. 11, 2018, P&G Docket No. 15231P and U.S. Pat. Appl. Pub. No. 2017/0246052, published on Aug. 31, 2017. The apertured nonwoven webs of the present disclosure may be used as nonwoven components of the absorbent article of FIG. 13, such as the topsheet or outer cover nonwoven material.

Absorbent Pad

Figure 14:
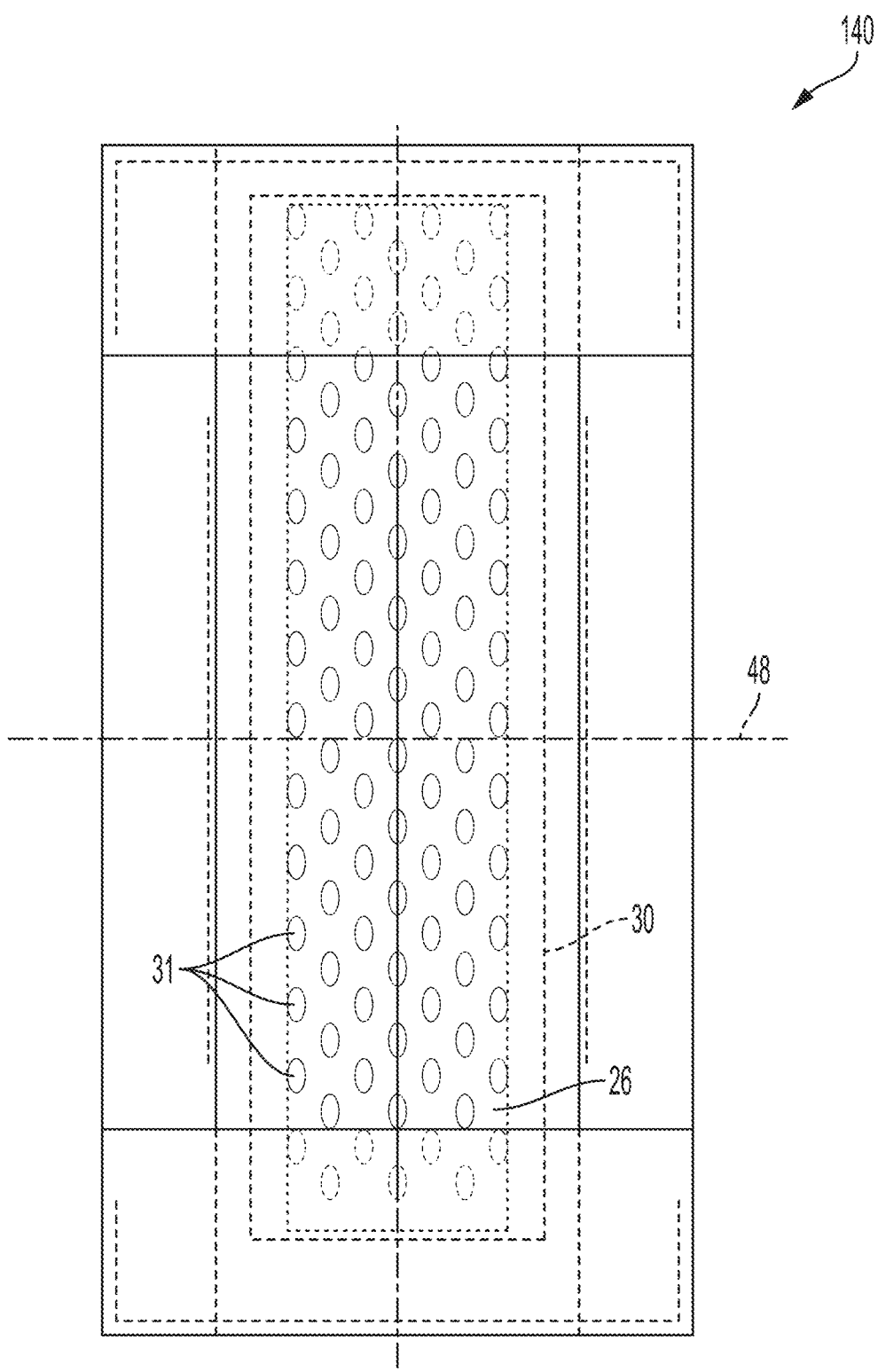
FIG. 14 is a plan view of an example absorbent article of the present disclosure that is an absorbent pad.

Referring to FIG. 14, an absorbent article of the present disclosure may be an absorbent pad 140. Elements of FIG. 14 having the same reference number as described above with respect to FIGS. 1-3 may be the same element (e.g., absorbent core 30). The absorbent pad 140 may comprise a liquid permeable topsheet 26, a liquid impermeable, or substantially liquid impermeable, backsheet, and an absorbent core 30. The liquid permeable topsheet 26 may define a plurality of apertures 31 and may be the apertured nonwoven web of the present disclosure. Absorbent pads may be used to contain bodily exudates from babies, including premature babies and Neonatal Abstinence Syndrome babies. The absorbent pads may be placed on a surface and then the babies may be laid on top of the absorbent pads. Suitable forms of absorbent pads are disclosed in U.S. Pat. Appl. Pub. Nos. 2017/0246044A1, published on Aug. 31, 2017 and 2017/0246053A1, published on Aug. 31, 2017.

Apertured Nonwoven Webs

Figure 15:
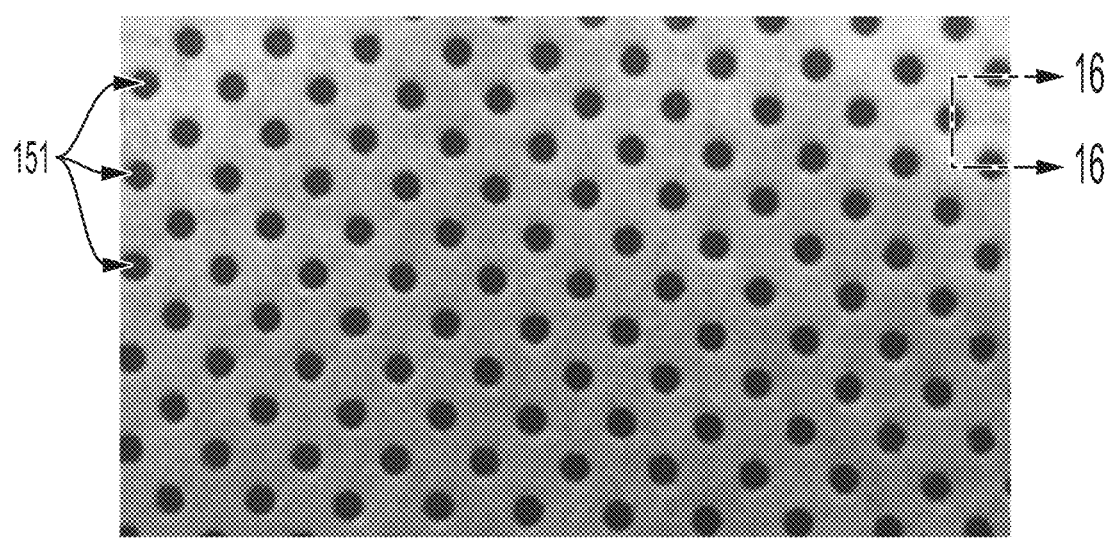
FIG. 15 is a schematic illustration of an apertured nonwoven web or topsheet of the present disclosure with apertures made by a punch process, representative of Examples 1, 2, 3, and 4.

FIG. 15 is a schematic illustration of an apertured nonwoven web or topsheet of Example 1. Referring to FIG. 15, the nonwoven web 150 may define a plurality of apertures 151. The plurality of apertures 151 may exhibit a highly regular geometric quality such that there is little variance in the shape of one aperture as compared to another aperture. For example, the nonwoven web 150 may have an aperture shape regularity of about 1% to about 12%, about 1% to about 10%, about 1% to about 8%, about 1% to about 6%, about 1.25% to about 5%, or about 1.5% to about 4.5%, specifically reciting all 0.1% increments within the specified ranges and all ranges formed therein or thereby, according to the Aperture Shape Regularity Test herein. This highly regular shape among the plurality of apertures 151 may be important both for visual quality as well as for robustness of the nonwoven web. Additionally, a nonwoven web comprising apertures exhibiting a high degree of shape regularity may exhibit improved bodily exudate transfer through the nonwoven web as compared to a nonwoven web comprising irregular apertures. Increased efficiency of bodily exudate transfer may allow the apertures to be smaller. Nonwoven webs comprising smaller apertures may be smoother and/or softer, especially in a topsheet context, where the nonwoven web may be placed against the skin of a wearer.

Referring again to FIG. 15, the plurality of apertures 151 may exhibit a highly regular geometric quality such that there is little variance in the size of one aperture as compared to another aperture. For example, the nonwoven web 150 may have an aperture size regularity of about 1% to about 15%, about 1% to about 12%, about 1% to about 10%, about 1% to about 8%, or about 1.5% to about 6%, specifically reciting all 0.1% increments within the specified ranges and all ranges formed therein or thereby, according to the Aperture Size Regularity Test herein. This highly regular size among the plurality of apertures 151 may be important both for visual quality as well as for robustness of the nonwoven web, especially during the process of manufacturing an absorbent article. Regularity in size among the plurality of apertures may aid in distribution of strain evenly across a nonwoven web, aiding in robustness while under strain during a manufacturing process. Additionally, a nonwoven web comprising apertures exhibiting a high degree of size regularity may exhibit improved bodily exudate transfer through the nonwoven web as compared to a nonwoven web comprising apertures of varying sizes. Increased efficiency of bodily exudate transfer may allow the apertures to be smaller. As discussed above, nonwoven webs comprising smaller apertures may be smoother and/or softer, especially in a topsheet context, where the nonwoven web may be placed against the skin of a wearer.

The apertured nonwoven web or apertured topsheet may define a second plurality of apertures, such that a first plurality of apertures and the second plurality of apertures form zones in the nonwoven web or topsheet. Each zone may comprise a plurality of apertures that may exhibit a highly regular geometric quality such that there is little variance in the shape and/or size of one aperture as compared to another aperture within the same zone, but the aperture size and/or shape varies between zones. A topsheet may, for example, define a first zone on a first side of a central lateral axis of an absorbent article, and a second zone on a second side of the central lateral axis. Suitable forms of nonwoven webs and topsheets comprising aperture zones are disclosed in U.S. Patent Application Publication No. 2016/0136014A1.

Figure 16:
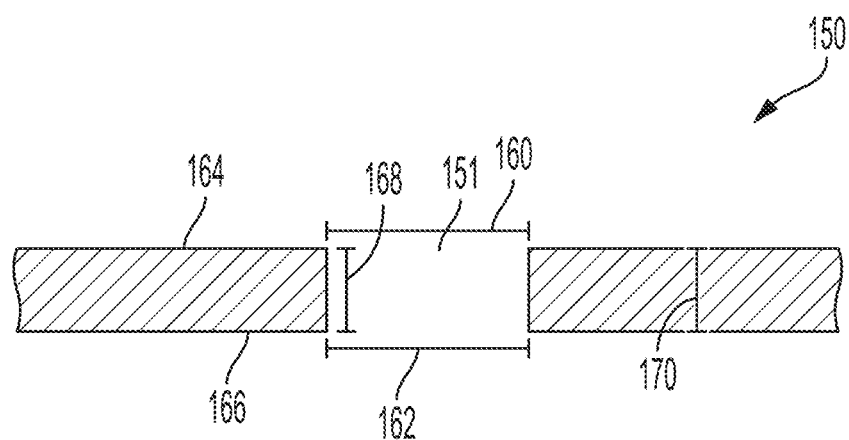
FIG. 16 is a cross-sectional schematic illustration of the apertured nonwoven web or topsheet taken about line 16-16 of FIG. 15.

FIG. 16 is a cross-sectional schematic illustration of the apertured nonwoven web 150 of FIG. 15, taken about line 16-16 of FIG. 15. The nonwoven web 150 may have a first side 164 and a second side 166. The apertures 151 may have a first side aperture size 160 in a plane generally parallel to the first side 164 that is substantially similar to, or about the same as, a second side aperture size 162 in a plane generally parallel to the second side 166. In such a fashion, the aperture size does not substantially decrease or increase from the first side to the second side of the nonwoven web 150. This may be true regardless of how many layers the nonwoven web comprises. A ratio of the first side aperture size 160 on the first side 164 to the second side aperture size 162 on the second side 164 may be between about 1.15:1 and about 1:1.15, about 1.10:1 and about 1:1.10, or about 1.05:1 and about 1:1.05, specifically reciting all 0.01 increments within the above-specified ranges and all ranges formed therein or thereby, according to the Aperture Size Ratio Test herein.

Figure 17:
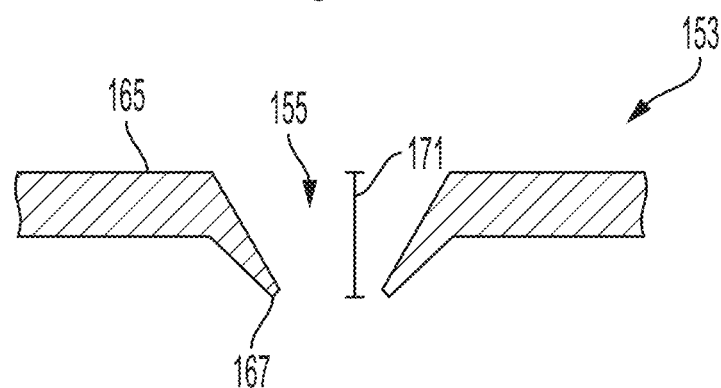
FIG. 17 is a cross-sectional schematic illustration of a related art conical apertured nonwoven web or topsheet illustrating an aperture comprising an aperture perimeter tail made by a hot pin aperturing method.

Referring to FIG. 17, a cross-sectional schematic illustration of a related art conical pin apertured nonwoven web 153 is provided. Apertures 155 are provided in the pin apertured nonwoven web 153. An apertured nonwoven web 153 in which the aperture size decreases from a first side 165 to a second side 167 of the nonwoven web 153 may have a reduced ability to quickly drain bodily exudates from the first side 165 of the pin apertured nonwoven web 153 to the second side 167. This may be important where a nonwoven web is used as, for example, a topsheet, and the functionality of an absorbent article depends on rapid delivery of the bodily exudates from the topsheet 26 to the acquisition material 38 or absorbent core material 30 below. This reduced ability to quickly drain fluid from a nonwoven web may be especially pronounced when the nonwoven web is hydrophobic. In the context of a topsheet comprising a hydrophobic top layer and a hydrophilic under layer, fluid, such as bodily exudates, may not be able to wick to an underlying hydrophilic layer due to the narrowing of the aperture from the wearer-facing surface down. Additionally, fluid flow may be restricted because the speed of fluid flow may be limited by the small size of the exit end of the aperture. Therefore, maintaining a relatively uniform aperture size from the first side 164 to the second side 166 of the nonwoven web 150 may allow bodily exudates to wick to layers underneath the nonwoven web 150, especially in applications when the nonwoven web 150 is utilized as a topsheet. The uniform aperture size on the first and second sides 164, 166 also allows fibers of a hydrophilic acquisition layer to extend into the apertures 151 for better acquisition of bodily exudates.

Figure 18:
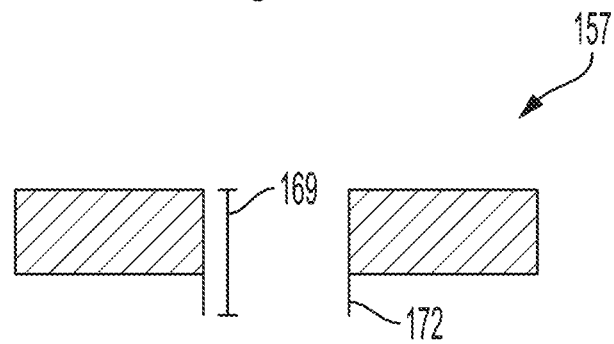
FIG. 18 is a cross-sectional schematic illustration of a related art apertured nonwoven web or topsheet illustrating an aperture made by a pin aperturing method.

Referring again to FIG. 16, the apertures 151 defined by the nonwoven web 150 may have an aperture wall thickness 168 between the first side 164 and the second side 166 that is not substantially larger than, or that is substantially similar to, the thickness of the nonwoven web in a non-apertured area 170 of the nonwoven web 150. In other words, the apertures may be substantially free of aperture perimeter tails 172, as shown on the illustration of related art apertured nonwoven web 157 of FIG. 18. These aperture perimeter tails 172 may form when portions of the nonwoven web that are moved to create the aperture remains partially attached to the web. This may cause the aperture wall thickness to be substantially larger than the thickness of the nonwoven web in a non-apertured area. The ratio of the aperture wall thickness 168 to the thickness of the nonwoven web 150 in a non-apertured area 170 may be between about 1:1 and about 1.5:1, about 1:1 and about 1.3:1, or about 1:1 and about 1.2:1, according to the Aperture Wall Thickness Ratio Test herein. When the nonwoven web 150 is utilized as a topsheet in an absorbent article, an aperture wall thickness 168 that is not substantially larger than the thickness of the nonwoven web 150 in a non-apertured area 170 may more easily allow for bodily exudates to wick to one or more layers underneath the nonwoven web. Further, when the nonwoven web 150 is utilized as a topsheet in an absorbent article, and the topsheet is hydrophobic, the hydrophobic nature of the aperture perimeter tails may create a hydrophobic environment within the apertures, preventing, or at least inhibiting, bodily exudate exit through the apertures and into hydrophilic layers underneath the nonwoven web. It is important to note the aperture wall thickness 169 of the related art nonwoven web 157 of FIG. 18 and the aperture wall thickness 171 of the nonwoven web 153 of FIG. 17 are larger than the aperture wall thickness of 168 of FIG. 16 of the present disclosure. In a topsheet context, the aperture tails place the topsheet further away from the acquisition material or absorbent core positioned below the topsheet, thereby potentially hindering suitable wicking of bodily exudates. The apertured nonwoven topsheet 150 of the present disclosure may have an aperture wall thickness 168 of between about 0.1 mm and about 0.75 mm, between about 0.2 mm and about 0.65 mm, or between about 0.25 mm and about 0.5 mm, according to the Aperture Wall Thickness Measurement Test herein.

Figure 19:
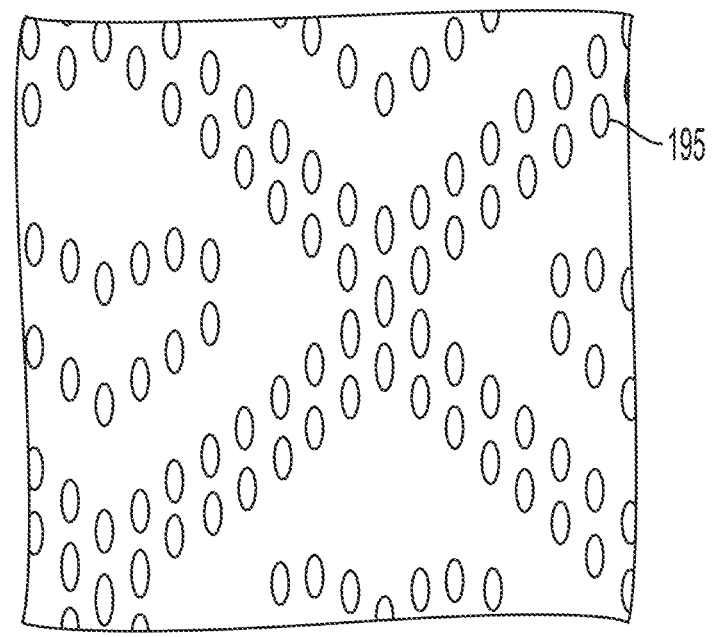
FIG. 19 is a schematic illustration of a nonwoven web apertured by an overbonding and ring rolling process, representative of Comparative Example 3.
Figure 20:
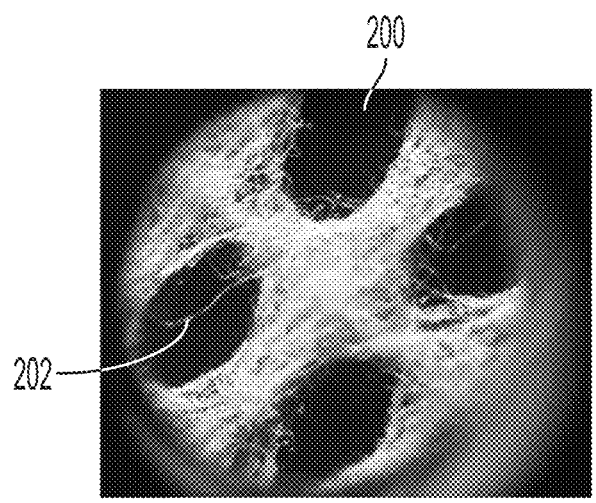
FIG. 20 is a magnified photograph of a related art nonwoven web apertured by a water jet process.
Figure 21:
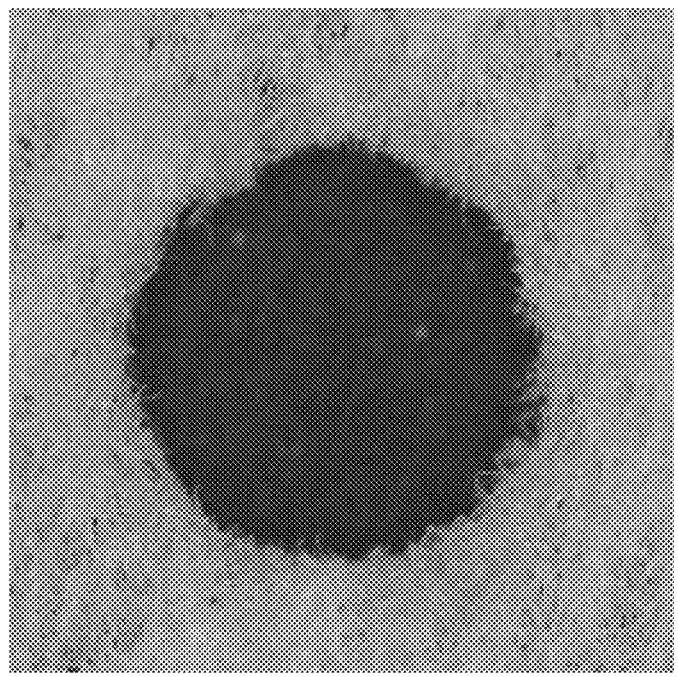
FIG. 21 is a magnified photograph of an apertured nonwoven web or topsheet of the present disclosure.

FIG. 19 is a schematic illustration of a related art nonwoven web apertured by an overbonding and ring rolling process as disclosed in U.S. Pat. No. 5,628,097 to Benson et al, issued on May 13, 1997. FIG. 20 is a magnified photograph of a related art nonwoven web apertured by a water jet punch process. FIG. 21 is a magnified photograph of an apertured nonwoven web of the present disclosure. The apertures of nonwoven web of the present disclosure may have improved aperture clarity as compared to those of the related art. In other words, the nonwoven web may be substantially free of fibers extending across or into the plurality of apertures. This provides for better bodily exudate acquisition in that the aperture opening is large enough to overcome the surface tension of the bodily exudate. Referring again to FIG. 19, the overbonding and ring rolling process of the related art may result patterned apertures 195 that exhibit stray fibers extending across, partially across, or into the apertures in that the process causes essentially cross-directional tearing of overbonds (i.e. densified regions). This may be due to tearing of the nonwoven web at the overbond locations during the ring rolling process. Referring now to FIG. 20, the resulting apertures 200 from the water jet punch process of the related art may also exhibit stray fibers 202 extending across the apertures. Referring again to FIG. 21, the apertures of the nonwoven webs or topsheets of the present disclosure having fewer or no stray fibers extending therethrough or thereacross may lead to improved bodily exudate acquisition, especially in a hydrophobic nonwoven topsheet context. If a hydrophobic fiber or fibers extend(s) across, partially across, or into an aperture, this may effectively reduce the size of the aperture to, for example, half of its size, and potentially cause reduced bodily exudate acquisition by providing an aperture opening that is too small to overcome the surface tension of the bodily exudate. As such, the plurality of apertures of the present disclosure may be between about 0.2% and about 3% occluded, between about 0.5% and about 2.75% occluded, or between about 0.75% and about 2.5% occluded, according to the Aperture Clarity Test as described below. Generally, apertures of related art nonwoven webs are greater than 3% occluded, according to the Aperture Clarity Test.

An absorbent article may comprise the apertured nonwoven webs or topsheets of the present disclosure. Where the topsheet has more than one layer, only the first layer on the first side configured to face a wearer may be apertured, with the apertured layer being hydrophobic and a second, unapertured layer, being hydrophilic. Alternatively, all layers of a multi-layered topsheet may be apertured. For example, a topsheet may comprise two apertured, hydrophobic nonwoven webs. In such case, the topsheet may be disposed in a face to face relationship with a hydrophilic acquisition layer. The topsheet may define a plurality of apertures over the entirety of the topsheet or may define a plurality of apertures over one or more discrete areas or zones of the topsheet. As an example, apertures may be formed only on the portion of the topsheet that overlaps the acquisition material or the absorbent core. The topsheet may comprise two or more zones which each define a plurality of apertures, the apertures exhibiting a high degree of regularity in shape and size within each zone, but having different sizes and/or different shapes between the zones. The apertures may also form any fanciful pattern in the topsheet.

EXAMPLES

Aperture Quality Measurements

Example 1 (FIG. 15): The apertured nonwoven web or topsheet of the present disclosure described as Example 1 is a two-layer nonwoven web laminate topsheet with punched apertures. The first (wearer-facing) layer is a 100% cotton nonwoven web produced by a spunlace process using hydroentangling. The second (garment-facing) layer is a 22 gsm carded ATB material made of 3 Denier per Filament (DPF) hydrophilic PE/PET fibers.

Figure 22:
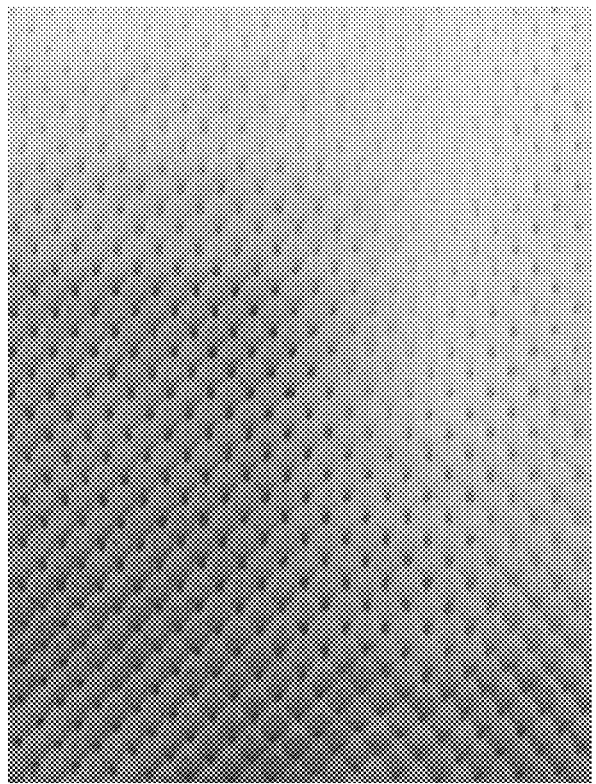
FIG. 22 is a photograph of a related art three dimensional nonwoven web topsheet with conical apertures made by a pin aperturing process, representative of Comparative Examples 1 and 5.

Comparative Example 1 (FIG. 22): The apertured nonwoven web or topsheet described as Comparative Example 1 is a 35 gsm air-through bonded three dimensional web with conical apertures formed by a male-female aperture emboss process. The fibers comprising the web have a core/sheath structure, where the core comprises polyethylene, and the sheath comprises polyethylene terephthalate.

Figure 23:
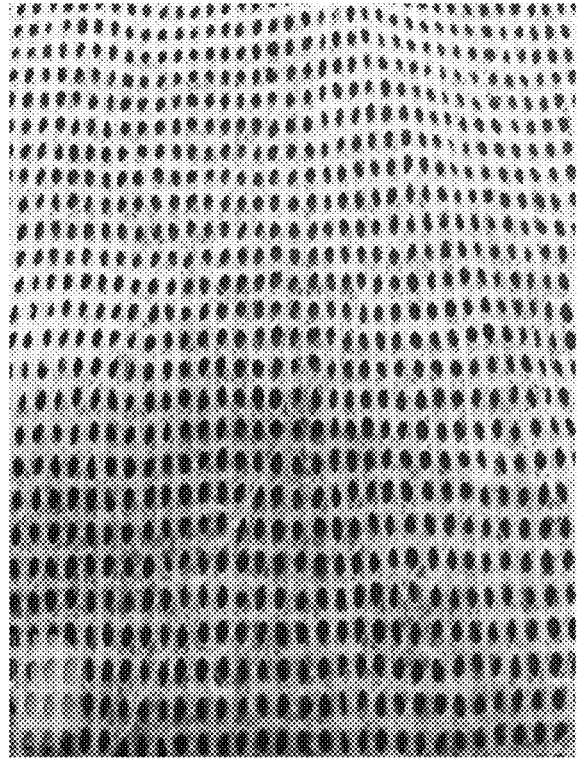
FIG. 23 is a photograph of a related art nonwoven web of Comparative Example 2 and Comparative Example 4.

Comparative Example 2 (FIG. 23): The apertured nonwoven web or topsheet described as Comparative Example 2 is a 100% cotton topsheet produced by a spunlace process. The topsheet has a basis weight of 35 gsm, and is an 8 mesh hydrophobic apertured nonwoven topsheet. Comparative Example 3 (FIG. 19): The apertured nonwoven web or topsheet described as Comparative Example 3 is a 35 gsm nonwoven web with apertures formed by an overbonding and ring rolling process. The fibers comprising the web have a core/sheath structure, wherein the core comprises polyethylene and the sheath comprises polyethylene terephthalate.

Example 1 and Comparative Examples 1-3 were analyzed for Aperture Quality according to the Aperture Quality tests presented below in the "Test Procedures" section. The results of this analysis are found in Table 1. The apertured nonwoven webs of the present disclosure have a lower Area RSD (measuring aperture size regularity), lower Aspect Ratio RSD (measuring aperture shape regularity), and lower Occlusion (measuring aperture clarity) as compared to the apertures of the comparative examples. Without wishing to be bound by theory, it is believed that improved aperture size regularity, aperture shape regularity, and aperture clarity may result in an apertured nonwoven web with improved bodily exudate handling performance and increased robustness during the manufacture of absorbent articles or apertured nonwoven webs.

TABLE 1

Aperture quality measurements of nonwoven topsheets taken from products

| Topsheet Sample 5 Replicates | | Aperture Size Regularity Area RSD (%) | Aperture Shape Regularity Aspect Ratio RSD (%) | Aperture Clarity Occlusion (%) |
|---|---|---|---|---|
| Example 1 | 1 | 3.72 | 2.68 | 1.57 |
| | 2 | 2.88 | 2.38 | 1.59 |
| | 3 | 4.87 | 2.82 | 2.04 |
| | 4 | 4.91 | 4.19 | 3.00 |
| | 5 | 4.21 | 2.29 | 1.72 |
| | Avg. | 4.12 | 2.87 | 1.98 |
| Comparative Example 1 | 1 | 23.65 | 20.87 | 4.03 |
| | 2 | 24.98 | 21.05 | 5.19 |
| | 3 | 26.98 | 24.06 | 4.48 |
| | 4 | 24.30 | 21.70 | 5.11 |
| | 5 | 26.35 | 22.75 | 4.05 |
| | Avg. | 25.25 | 22.09 | 4.57 |
| Comparative Example 2 | 1 | 19.01 | 18.00 | 3.45 |
| | 2 | 21.84 | 24.05 | 2.90 |
| | 3 | 24.64 | 20.59 | 2.81 |
| | 4 | 21.97 | 18.27 | 3.89 |
| | 5 | 20.55 | 17.13 | 4.22 |
| | Ave | 21.60 | 19.61 | 3.45 |
| Comparative Example 3 | 1 | 46.08 | 32.05 | 5.46 |
| | 2 | 44.34 | 37.07 | 5.46 |
| | 3 | 26.44 | 26.65 | 5.10 |
| | 4 | 36.83 | 43.71 | 3.20 |
| | 5 | 33.88 | 21.51 | 4.85 |
| | Ave | 37.51 | 32.20 | 4.81 |

Fluid Handling Performance Measurements

Example 2 (FIG. 15): The apertured nonwoven web or topsheet of the present disclosure described in Example 2 is a 100% hydrophobic flat apertured cotton topsheet with the apertures being punched. The first layer is 100% hydrophobic cotton spunlace nonwoven web with a basis weight of 35 gsm. The second layer is a 22 gsm basis weight air-through nonwoven web made of 40% 2 dpf hydrophobic and 60% 3dpf hydrophilic PE/PET fibers.

Example 3 (FIG. 15): The apertured nonwoven web or topsheet of the present disclosure described in Example 3 is a 100% hydrophobic flat apertured spunlace nonwoven cotton topsheet with the apertures being punched. The first layer is 100% hydrophobic cotton fibers with a basis weight of 35 gsm. The second layer is a 22 gsm basis weight air-through nonwoven web made of 3 dpf hydrophilic PE/PET fibers.

Example 4 (FIG. 15): The apertured nonwoven web or topsheet of the present disclosure described in Example 4 is a 100% hydrophobic flat apertured spunlace nonwoven cotton topsheet with the apertures being punched. The topsheet is a single layer of 35 gsm basis weight that is hydrophobic and that comprised 100% cotton fibers.

Comparative Example 4 (FIG. 23): The topsheet described as Comparative Example 4 is a 100% cotton topsheet produced by a spunlace process. The topsheet has a basis weight of 35 gsm and is an 8 mesh hydrophobic apertured nonwoven topsheet.

Comparative Example 5 (FIG. 22): The topsheet described as Comparative Example 5 is a three-dimensional 100% cotton topsheet with conical apertures formed by a male-female embossing process, from Yanjan Nonwovens. The top layer comprises 100% hydrophobic cotton fibers and has a basis weight of 35 gsm. The second layer is a hydrophilic 40 gsm basis weight carded air-through nonwoven made of PE/PET fibers.

Examples 2-4 and Comparative Examples 4-5 were analyzed for Fluid Handling Performance according to the Fluid Handling Performance tests presented below in the "Test Procedures" section. The results of this analysis are found in Table 2. Examples 2-4 have RunOff scores of less than 20%, while maintaining Rewet scores of less than 0.15 g. Comparative Example 4 received a Run-Off score of 4.25%, but received a Rewet score of 0.23 g, higher than the Rewet scores of Examples 2-4. Comparative Example 5, on the other hand, received a Rewet score of 0.09 g, but had a relatively high Run-Off score of 58.58%. Without wishing to be bound by theory, it is believed that improved aperture shape and size regularity and improved aperture clarity may improve Run-Off scores without the need to increase the Opening Rate of a topsheet. Increasing Opening Rate, typically by increasing the size of apertures, may increase fluid permeation through the topsheet, thus decreasing Run-Off. Increasing Opening Rate, however, may result in increased Rewet scores because the larger Opening Rate provides greater area for a fluid to re-enter a topsheet (i.e. Rewet). Therefore, by improving aperture shape and size regularity and aperture clarity of a topsheet, nonwoven topsheets may maintain both low Run-Off and low Rewet scores.

TABLE 2

Fluid handling performance measurements of nonwoven topsheets

| Example | Run-Off [%] | Rewet [g] | Fluid Strike Through [s] | Opening Rate [%] |
|---|---|---|---|---|
| Example 2 | 15.30 | 0.11 | 2.81 | 18.10 |
| Example 3 | 7.47 | 0.07 | 3.46 | 18.39 |
| Example 4 | 15.31 | 0.12 | 4.90 | 18.77 |
| Comparative Example 4 | 4.25 | 0.23 | 2.71 | 24.71 |
| Comparative Example 5 | 58.58 | 0.09 | 3.08 | 7.59 |

Method of Manufacturing Apertured Nonwoven Webs or Topsheet

Figure 24:
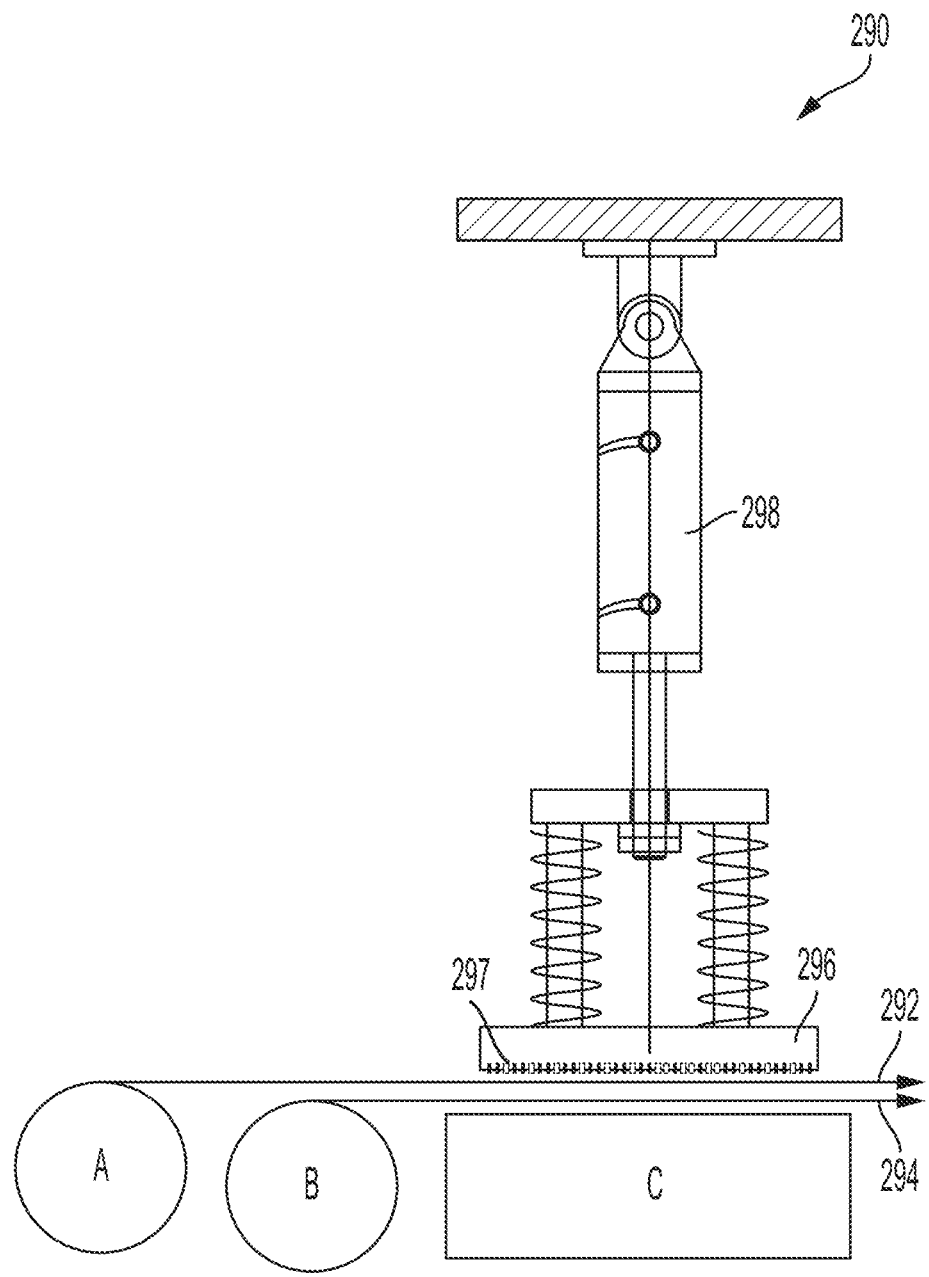
FIG. 24 is a schematic illustration of an apparatus for forming apertures of the present disclosure.

The apertured nonwoven webs or topsheets of the present disclosure may be made generally by the process schematically illustrated in FIG. 24. First, a precursor nonwoven web 292 is fed, together with consumable material 294, into the punch unit 296 in a face-to-face manner. The precursor nonwoven web 292 may be unwound from roll A. The consumable material 294 may be unwound from roll B. The consumable material 294 may be of a greater stiffness than the precursor nonwoven web 292 and may be used to increase the stiffness of the precursor nonwoven web 292 during the aperturing process. The consumable material 294 may be, for example, paperboard with a stiffness greater than that of the precursor nonwoven web 292. This increase in stiffness may allow for creation of cleaner, more regular apertures with fewer, or no, aperture perimeter tails as compared to related art aperturing processes. In another example, the consumable material 294 may be replaced with an acquisition layer, wherein the precursor nonwoven web 292 and the acquisition layer may be unwound from their respective rolls and bonded together to form a laminate prior to entry into the punch unit 296. An actuator 298, such as a pneumatic actuator, for example, moves the punch unit 296, comprising a plurality of punch components 297, toward the precursor web to create apertures in the nonwoven web 292 and the consumable material 294. Punched pieces may then be at least partially removed, or fully removed, by directing a fluid, for example air, over the nonwoven web, or by placing the nonwoven web under vacuum (box C) after creation of the apertures in the nonwoven web. After the aperturing is complete, the nonwoven web may be wound or conveyed directly into a manufacturing operation for a consumer product, such as an absorbent article.

Test Procedures

Aperture Quality Tests

Preparation of Nonwoven Topsheet Samples

If a topsheet or nonwoven web is available in its raw material form, a specimen with the size of 80 mm×80 mm is cut from the raw material. Otherwise, a topsheet specimen is removed from the absorbent article, centered at the intersection of the longitudinal and lateral centerlines of the absorbent article. For the purpose of removing the topsheet from the absorbent article, a razor blade is used to excise the topsheet from the underling layers of the absorbent article around the outer perimeter for the area of 80 mm×80 mm. A cryogenic spray (such as Cyto-Freeze, Control Company, Houston TX) may be used to remove the topsheet specimen from the underling layers, if necessary.

Aperture Quality Test on Nonwoven Topsheet Materials or Nonwoven Webs

Aperture Size Regularity, Aperture Shape Regularity and Aperture Clarity measurements for a nonwoven topsheet or nonwoven web are performed on images generated by placing the specimen flat against a dark background under uniform surface lighting conditions and acquiring a digital image using an optical microscope such as Keyence 3D Measurement System VR-3200 or equivalent. Analyses are performed using ImageJ software (version 1.52e or above, National Institutes of Health, USA) and calibrated against a ruler certified by NIST or equivalent. The image needs to be distance calibrated with an image of the ruler to give an image resolution, i.e. 67.8 pixels per mm. The microscope acquires a specimen image with a field of view size of 50 mm×50 mm after performing an auto-focus step.

Open a specimen image in ImageJ. Set the scale according to the image resolution. Convert the image type to 8 bit. The 8-bit grayscale image is then converted to a binary image (with "black" foreground pixels corresponding to the aperture regions) using the "Minimum" thresholding method: If the histogram of gray level (GL) values (ranging from 0 to 255, one bin with propensity $P_i$ per gray level i) has exactly two local maxima, the threshold gray level value t is defined as that value for which $P_{t-1} > P_t$ and $P_t P_{t+1}$. If the histogram has greater than two local maxima, the histogram is iteratively smoothed using a windowed arithmetic mean of size 3, and this smoothing is performed iteratively until exactly two local maxima exist. The threshold gray level value t is defined as that value for which $P_{t-1} > P_t$ and $P_t \leq P_{t+1}$. This procedure identifies the gray level (GL) value for the minimum population located between the dark pixel peak of the aperture holes and the lighter pixel peak of the specimen material. If the histogram contains either zero or one local maximum, the method cannot proceed further, and no output parameters are defined.

(1) Aperture Size Regularity and Aperture Shape Regularity

Set the measurements to include the analysis of Area and Shape Descriptors (i.e. Aspect Ratio of a fitted ellipse). Select the Analyze Particles function. Set the analysis to include holes and exclude the edge openings and small openings with size below 0.30 mm². The percent Relative Standard Deviation (percent RSD, defined as the Standard Deviation divided by the Mean and multiplied by 100) of the Area values for all the selected openings is calculated to give the factor of Aperture Size Regularity to the nearest 0.01%. The percent Relative Standard Deviation (percent RSD, defined as the Standard Deviation divided by the Mean and multiplied by 100) of the Aspect Ratio values for all the selected openings is calculated to give the factor of Aperture Shape Regularity to the nearest 0.01%. If a repeating pattern of apertures having different shapes or sizes exists, then a classification based on visual inspection should be performed to group together equivalent apertures prior to calculation of the percent RSD values and the largest percent RSD value reported.

(2) Aperture Clarity Aperture Clarity is determined by the measurement of percent Occlusion (i.e. the percentage of the aperture area occluded by stray fibers.) Create a filtered image by removing small openings in the binary image using an outlier removing median filter, which replaces a pixel with the median of the surrounding area of 6 pixels in radius if the pixel is darker than the surrounding. Remove the stray fibers from apertures using a morphological closing filter, which performs a dilation operation followed by an erosion operation under the settings of one adjacent foreground (or background) pixel for dilation (or erosion) and pad edges when eroding, before filling the remaining holes in the apertures. Subtract the original binary image from the filtered image, keeping only positive values to show the stray fibers within apertures and measure the total Area of stray fibers. The total Area of stray fibers is then divided by the total Area of apertures from the filtered image and multiplied by 100 to give the result of percent Occlusion reported as Aperture Clarity to the nearest 0.01%.

Prepare and analyze a total of five substantially similar replicate samples. The reported values will be the arithmetic mean of the five replicate samples to the precision described above.

Aperture Size Ratio Test, Aperture Wall Thickness Measurement Test, and Aperture Wall Thickness Ratio Test The Aperture Size Ratio Test, Aperture Wall Thickness Measurement Test, and Aperture Wall Thickness Ratio Test measurements for a nonwoven topsheet or nonwoven web are performed on images generated by Scanning Electron Microscopy. To obtain cross-section images of apertured nonwovens, a 10 mm×3 mm cross-section specimen cutting through at least one aperture is prepared using a razor blade. When a specimen is obtained from an absorbent article, a 10 mm×3 mm cross-section specimen cutting through at least one aperture is excised using a razor blade and removed from the absorbent article carefully not to impart any contamination or distortion to the test specimen layer during the process. A cryogenic spray (such as Cyto-Freeze, Control Company, Houston TX) may be used to remove a topsheet, or a topsheet and a secondary topsheet together, from the underlying layers in the absorbent article, if necessary.

SEM images of specimens are taken using a Scanning Electron Microscope (SEM) such as Tabletop Microscope TM3000 (Hitachi, Japan) or equivalent. The specimen is mounted vertically on a sample stage using carbon tape for cross-section imaging. Then the specimen is sputtered with platinum to avoid electric charging and improve overall conductivity under the conditions of 15 mA current and 120 second coating time. The platinum-coated specimen is subsequently transferred into the SEM specimen chamber for the measurements under vacuum.

An appropriate magnification and working distance are chosen such that the aperture cross-section is suitably enlarged for measurement. The cross-sectional edge of the specimen is oriented such that it is substantially aligned to the horizontal direction. The aperture and a portion of adjacent non-apertured area is imaged at an acceleration voltage of 5 kV, and saved as an 8 bit jpeg image containing a linear distance scale for calibration.

Figure 25:
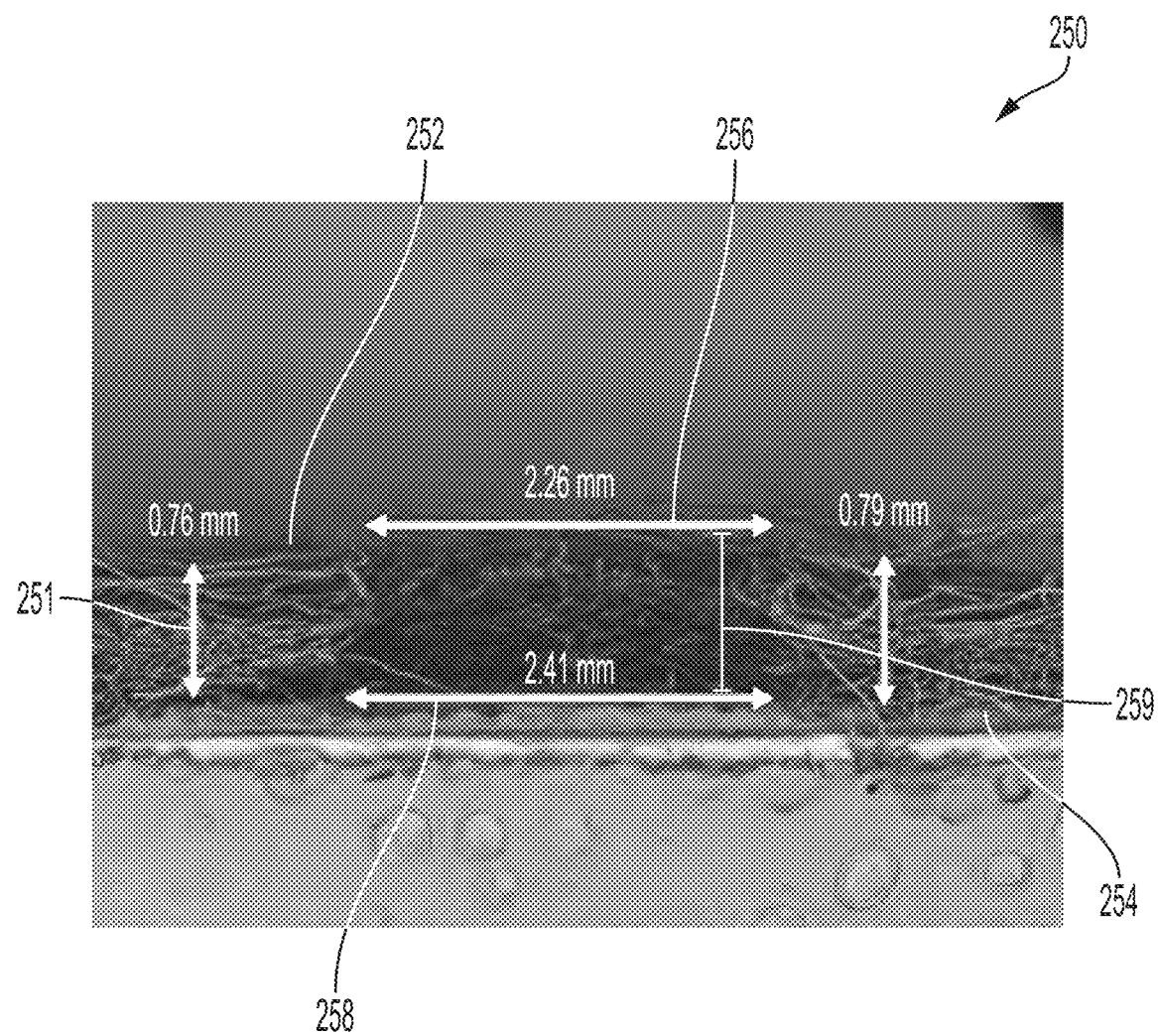
FIG. 25 is a magnified photograph of a cross-section specimen of the apertured nonwoven web described herein as Example 1.

The image is analyzed using ImageJ software (version 1.52e or above, National Institutes of Health, USA) to measure the aperture size, aperture wall thickness, and the specimen thickness in a non-aperture area. FIG. 25 is an image of the nonwoven web 250 described herein as Example 1. The nonwoven web 250 has a first side 252 and a second side 254. The first side aperture size 256 is the measured distance across the aperture on the first side 252, and the second side aperture size 258 is the measured distance across the aperture on the second side 254. Aperture Wall Thickness 259 is the measured distance between the first 252 and second 254 sides of the specimen within the aperture, as shown in FIG. 25. The specimen thickness 251 is measured as the distance between the first 252 and second 254 sides of the specimen in a non-apertured area. All measurements are recorded to the nearest 0.01 mm.

Aperture Size Ratio Test:

Measure the aperture size on the first side and the second side of the specimen, as described above. The Aperture Size Ratio is calculated as the ratio of the first side aperture size to the second side aperture size.

Aperture Wall Thickness Measurement Test:

Measure the aperture wall thickness as described above. The Aperture Wall Thickness Measurement is the result of this measurement.

Aperture Wall Thickness Ratio Test:

Measure the aperture wall thickness and the specimen thickness, as described above. Aperture Wall Thickness Ratio is calculated as the ratio of aperture wall thickness to the thickness between the first side and the second side of the topsheet in a non-aperture area.

Fluid Handling Performance Tests

Run-Off Test:

Run-Off is measured according to basic method for testing hydrophilic nonwovens in WSP 80.9 (05), standard test method for nonwoven run-off. The inclination angle is set to be 25°+/−1°. A total mass of test liquid of 25±0.5 g is used.

The topsheet sample is removed from the absorbent article, centered at the intersection of the longitudinal and lateral centerlines of the absorbent article: for the purpose of removing the topsheet from the absorbent article, a razor blade is used to excise the topsheet from the underling layers of the absorbent article around the outer perimeter of the 100 mm×280 mm area. The specimen is carefully removed such that its longitudinal and lateral extension are maintained. A cryogenic spray (such as Cyto-Freeze, Control Company, Houston TX) can be used to remove the topsheet specimen from the underling layers, if necessary. The topsheet layer with 100 mm width is centered over the two 140 mm wide layers of reference filter paper.

If the dimensions of the absorbent article do not allow to excise an area of 100 mm×280 mm, then the largest possible rectangular topsheet area will be excised from the absorbent article with the procedure above. Multiple specimens will be removed from multiple absorbent articles and will be connected to each other with a 5 mm wide overlap on each neighboring side between two separate pieces. A double tape adhesive will be placed in the 5 mm wide overlap area, between the two layers being stitched together. This procedure will allow to create a 100 mm×280 mm area to be used according to basic method for testing hydrophilic nonwovens in WSP 80.9 procedure. For the testing, the tube, supplying the test liquid, will be placed between any overlap areas, in machine direction or cross direction.

Rewet Test:

Rewet is measured according to basic method for testing hydrophilic nonwovens in WSP 80.10-09, standard test method for nonwoven rewet.

If a topsheet is available in its raw material form, a specimen 125 mm±0.5 mm in length and 125 mm±0.5 wide is cut from the raw material according to WSP 80.10-09. Otherwise, a topsheet sample is removed from the absorbent article, centered at the intersection of the longitudinal and lateral centerlines of the absorbent article: for the purpose of removing the topsheet from the absorbent article, a razor blade is used to excise the topsheet from the underling layers of the absorbent article around the outer perimeter of the 125 mm×125 mm area. The specimen is carefully removed such that its longitudinal and lateral extension are maintained. A cryogenic spray (such as Cyto-Freeze, Control Company, Houston TX) can be used to remove the topsheet specimen from the underling layers, if necessary.

Fluid Strike Through Test:

Fluid Strike Through is measured according to the WSP 70.3-80 standard test method for nonwoven fluid Strike Through.

If a topsheet is available in its raw material form, a specimen 125 mm±0.5 mm in length and 125 mm±0.5 mm wide is cut from the raw material according to WSP 70.3-08. Otherwise, a topsheet sample is removed from the absorbent article, centered at the intersection of the longitudinal and lateral centerlines of the absorbent article. For the purposes of removing the topsheet from the absorbent article, a razorblade is used to excise the topsheet from the underlying layers of the absorbent article around the outer perimeter of the 125 mm±0.5 mm area. The specimen is carefully removed such that its longitudinal and lateral extension are maintained. A cryogenic spray (such as Cyto-Freeze, Control Company, Huston, TX) can be used to remove the topsheet specimen from the underlying layers, if necessary.

Opening Rate Test:

Set the measurements to include the analysis of Area. Select the Analyze Particles function. Set the analysis to include holes and the edge openings but exclude small openings with a size below 0.30 mm². The Opening Rate (%) is calculated to the nearest 0.01%, by dividing the sum of the open area values of both full and partial openings by the image by the total area of the field of view in the image.

Combinations

A. A nonwoven topsheet for an absorbent article, the nonwoven topsheet comprising:
  carded fibers;
  a first side; and
  a second side;
  wherein the topsheet defines a plurality of apertures;
  wherein the apertures each have a first side aperture size and a second side aperture size, wherein a ratio of the first side aperture size to the second side aperture size is between about 1.15:1 and about 1:1.15, preferably between about 1.10:1 and about 1:1.10, more preferably between about 1.05:1 and about 1:1.05, according to the Aperture Size Ratio Test;
  wherein the plurality of apertures have an aperture size regularity of about 1% to about 15%, preferably between about 1.5% to about 12%, and more preferably between about 2% and about 10%, according to the Aperture Size Regularity Test; and
  wherein the plurality of apertures have an aperture shape regularity of between about 1% to about 12%, preferably between about 1% to about 8%, and more preferably between about 1.5% to about 4.5%, according to the Aperture Shape Regularity Test.

B. The nonwoven topsheet of Paragraph A, comprising:
  a first nonwoven layer comprising the carded fibers, wherein the first nonwoven layer forms the first side; and
  a second nonwoven layer joined to the first nonwoven layer, wherein the second nonwoven layer forms the second side.

C. The nonwoven topsheet of Paragraph B, wherein the first nonwoven layer is naturally hydrophobic.

D. The nonwoven topsheet of Paragraphs B, wherein the first side is treated to be hydrophobic.

E. The nonwoven topsheet of Paragraphs B, wherein the first nonwoven layer is treated to be hydrophobic.

F. The nonwoven topsheet of any one of Paragraphs B-E, wherein the second nonwoven layer is hydrophilic.

G. The nonwoven topsheet of any one of Paragraphs B-F, wherein the second nonwoven layer comprises synthetic fibers.

H. The nonwoven topsheet of any one of Paragraphs B-G, wherein the second nonwoven layer comprises natural fibers.

I. The nonwoven topsheet of any one of Paragraphs B-H, wherein the second nonwoven layer comprises bi-component fibers comprising a first polymer component and a second polymer component.

J. The nonwoven topsheet of Paragraph I, wherein the first polymer component comprises polyethylene, and wherein the second polymer component comprises polyethylene terephthalate.

K. The nonwoven topsheet of any one of the preceding paragraphs, wherein the carded fibers comprise natural fibers.

L. The nonwoven topsheet of any one of the preceding paragraphs, wherein the carded fibers comprise cotton fibers.

M. The nonwoven topsheet of any one of the preceding paragraphs, wherein the plurality of apertures are between about 0.2% and about 3% occluded, preferably between about 0.4% and about 2.75% occluded, and more preferably between about 0.5% and about 2.5% occluded, according to the Aperture Clarity Test.

N. The nonwoven topsheet of any one of any one of the preceding paragraphs, wherein the apertures each have an aperture wall thickness between the first side and the second side, and wherein a ratio of the aperture wall thickness to a thickness between the first side and the second side of the topsheet in a non-aperture area is between about 1:1 and about 1.5:1, preferably between about 1:1 and about 1.3:1, and more preferably between about 1:1 and about 1.2:1, according to the Aperture Wall Thickness Ratio Test.

O. The nonwoven topsheet of any one of the preceding paragraphs, wherein the apertures have an aperture wall thickness of between about 0.1 mm and about 0.75 mm, preferably between about 0.2 mm and about 0.65 mm, and more preferably between about 0.25 mm and about 0.5 according to the Aperture Wall Thickness Measurement Test.

P. The nonwoven topsheet of any one of any one of the preceding paragraphs, wherein the topsheet has a Run-Off in the range of about 1% to about 25%, preferably between about 2% and about 20%, and more preferably between about 4% and about 18% according to the Run-Off Test.

Q. The nonwoven topsheet of any one of the preceding paragraphs, wherein the topsheet has a Rewet in the range of between about 0.01 g and about 0.5 g, more preferably between about 0.03 g and about 0.3 g, and more preferably between about 0.05 g and about 0.2 g, according to the Rewet Test.

R. The nonwoven topsheet of any one of any one of the preceding paragraphs, wherein the topsheet has a Fluid Strike Through between about 1 s to about 6.5 s, preferably between about 1.5 s and about 6 s, and more preferably between about 2 s and about 5 s, according to the fluid Strike Through Test.

S. The nonwoven topsheet of any one of any one of the preceding paragraphs, wherein perimeters of the apertures are substantially free of aperture perimeter tails.

T. An absorbent article comprising:
the nonwoven topsheet of any one of the preceding paragraphs;
a liquid impermeable backsheet; and
an absorbent core positioned intermediate the nonwoven topsheet and the backsheet.

U. An acquisition layer and topsheet laminate for an absorbent article, the laminate comprising:
the nonwoven topsheet of any one of Paragraphs A-S; and
an acquisition layer.

V An acquisition layer and topsheet laminate for an absorbent article, the laminate comprising:
a topsheet comprising:
carded fibers;
a first side;
a second side;
wherein the topsheet defines a plurality of apertures;
wherein the apertures each have a first side aperture size and a second side aperture size, and wherein a ratio of the first side aperture size to the second side aperture size is between about 1.15:1 and about 1:1.15, preferably between about 1.10:1 and about 1:1.10, more preferably between about 1.05:1 and about 1:1.05, according to the Aperture Size Ratio Test;
wherein the plurality of apertures have an aperture size regularity of about 1% to about 15%, preferably between about 1.5% to about 12%, and more preferably between about 2% and about 10%, according to the Aperture Size Regularity Test;
wherein perimeters of the apertures are substantially free of aperture tails;
wherein the apertures have a shape regularity between about 1% and about 12%, preferably between about 1.5% and about 8%, and more preferably between about 1.8% and about 6%, according to the Aperture Shape Regularity Test; and
an acquisition layer, wherein the acquisition layer is hydrophilic.

W. The laminate of Paragraph V, wherein the topsheet comprises:
a first nonwoven layer comprising the carded fibers, wherein the first nonwoven layer forms the first side; and
a second nonwoven layer joined to the first layer, wherein the second nonwoven layer forms the second side.

X. The laminate of Paragraph W, wherein the first nonwoven layer is hydrophobic.

Y The laminate of any one of Paragraphs W-X, wherein the carded fibers comprise cotton fibers.

Z. The laminate of any one of Paragraphs V-Y, wherein the plurality of apertures are between about 0.2% and about 3% occluded, preferably between about 0.4% and about 2.75% occluded, and more preferably between about 0.5% and about 2.5% occluded, according to the Aperture Clarity Test.

AA. The laminate of any one of Paragraphs V-Z, wherein the apertures each have an aperture wall thickness between the first and second sides, and wherein a ratio of the aperture wall thickness to a thickness between the first and second sides of the topsheet in a non-aperture area is between about 1:1 and about 1.5:1, preferably between about 1:1 and about 1.3:1, and more preferably between about 1:1 and about 1.2:1, according to the Aperture Wall Thickness Ratio Test.

BB. The laminate of any one of Paragraphs V-AA, wherein the topsheet has a Run-Off in the range of about 1% to about 25%, preferably between about 2% and about 20%, and more preferably between about 4% and about 18% according to the Run-Off Test.

CC. The laminate of any one of Paragraphs V-BB, wherein the topsheet has a Rewet in the range of between about 0.01 g and about 0.5 g, more preferably between about 0.03 g and about 0.3 g, and more preferably between about 0.05 g and about 0.2 g, according to the Rewet Test.

DD. The laminate of any one of Paragraphs V-CC, wherein the topsheet has a Fluid Strike Through between about 1 s to about 6.5 s, preferably between about 1.5 s and about 6 s, and more preferably between about 2 s and about 5 s, according to the Fluid Strike Through Test.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article comprising:
a nonwoven topsheet:
a liquid impermeable backsheet; and
an absorbent core positioned at least partially intermediate the topsheet and the backsheet;
wherein the topsheet comprises:
carded fibers;
a first side; and
a second side;
wherein the topsheet defines a plurality of apertures;
wherein the apertures each have a first side aperture size and a second side aperture size, wherein a ratio of the first side aperture size to the second side aperture size is between about 1.05:1 and about 1:1.05, according to the Aperture Size Ratio Test;

wherein the plurality of apertures have an aperture size regularity of about 1.5% to about 6%, according to the Aperture Size Regularity Test;

wherein the plurality of apertures have an aperture shape regularity of between about 1.5% to about 4.5%, according to the Aperture Shape Regularity Test; and wherein the topsheet has an opening rate of between 10% and 20%, according to the Opening Rate test.

2. The absorbent article of claim 1, wherein the topsheet comprises:

a first nonwoven layer comprising the carded fibers, wherein the first nonwoven layer forms the first side; and a second nonwoven layer joined to the first nonwoven layer, wherein the second nonwoven layer forms the second side.

3. The absorbent article of claim 2, wherein the first nonwoven layer is naturally hydrophobic.

4. The absorbent article of claim 2, wherein the first nonwoven layer is treated to be hydrophobic.

5. The absorbent article of claim 1, wherein the carded fibers comprise natural fibers.

6. The absorbent article of claim 1, wherein the carded fibers comprise cotton fibers.

7. The absorbent article of claim 2, wherein the second nonwoven layer is hydrophilic.

8. The absorbent article of claim 2, wherein the second nonwoven layer comprises synthetic fibers.

9. The absorbent article of claim 1, wherein perimeters of the apertures are substantially free of aperture perimeter tails.

10. The absorbent article of claim 1, wherein the plurality of apertures are between about 0.75% and about 2.5% occluded, according to the Aperture Clarity Test.

11. The absorbent article of claim 1, wherein the apertures each have an aperture wall thickness between the first side and the second side, and wherein a ratio of the aperture wall thickness to a thickness between the first side and the second side of the topsheet in a non-aperture area is between about 1:1 and about 1.5:1, according to the Aperture Wall Thickness Ratio Test.

12. The absorbent article of claim 1, wherein the apertures have an aperture wall thickness of between about 0.1 mm and about 0.75 mm, according to the Aperture Wall Thickness Measurement Test.

13. The absorbent article of claim 1, wherein the topsheet has a Rewet in the range of between about 0.01 g and about 0.5 g, according to the Rewet Test.

14. The absorbent article of claim 1, wherein the topsheet has a Run-Off in the range of about 1% to about 25%, according to the Run-Off Test.

15. The absorbent article of claim 1, wherein the topsheet has a Fluid Strike Through between about 1 s to about 6.5 s, according to the Fluid Strike Through Test.

16. An absorbent article comprising:
a nonwoven topsheet:
a liquid impermeable backsheet; and
an absorbent core positioned at least partially intermediate the topsheet and the backsheet;

wherein the topsheet comprises:
a first nonwoven layer comprising carded fibers, wherein the first nonwoven layer is hydrophobic and forms a first side; and
a second nonwoven layer joined to the first nonwoven layer, wherein the second nonwoven layer is hydrophilic and forms a second side;

wherein the topsheet defines a plurality of apertures;

wherein the apertures each have a first side aperture size and a second side aperture size, wherein a ratio of the first side aperture size to the second side aperture size is between about 1.05:1 and about 1:1.05, according to the Aperture Size Ratio Test;

wherein the plurality of apertures have an aperture size regularity of about 1.5% to about 6%, according to the Aperture Size Regularity Test;

wherein the plurality of apertures have an aperture shape regularity of between about 1.5% to about 4.5%, according to the Aperture Shape Regularity Test; and wherein the topsheet has an opening rate of between 10% and 20%, according to the Opening Rate test.

17. The absorbent article of claim 16, wherein the carded fibers comprises cotton fibers.

18. The absorbent article of claim 16, wherein the second nonwoven layer comprises synthetic fibers.

19. The absorbent article of claim 16, wherein the plurality of apertures are between about 0.75% and about 2.5% occluded, according to the Aperture Clarity Test.

20. An absorbent article comprising:
a nonwoven topsheet:
a liquid impermeable backsheet;
an absorbent core positioned at least partially intermediate the topsheet and the backsheet; and
an acquisition layer;

wherein the acquisition layer and the nonwoven topsheet are in a face-to-face relationship and form a laminate;

wherein the topsheet comprises:
a first nonwoven layer comprising carded cotton fibers, wherein the first nonwoven layer is hydrophobic and forms a first side; and
a second nonwoven layer joined to the first nonwoven layer, wherein the second nonwoven layer is hydrophilic and forms a second side;

wherein the topsheet defines a plurality of apertures;

wherein the apertures each have a first side aperture size and a second side aperture size, wherein a ratio of the first side aperture size to the second side aperture size is between about 1.05:1 and about 1:1.05, according to the Aperture Size Ratio Test;

wherein the plurality of apertures have an aperture size regularity of about 1.5% to about 6%, according to the Aperture Size Regularity Test;

wherein the plurality of apertures have an aperture shape regularity of between about 1.5% to about 4.5%, according to the Aperture Shape Regularity Test;

wherein the plurality of apertures are between about 0.75% and about 2.5% occluded, according to the Aperture Clarity Test; and wherein the topsheet has an opening rate of between 10% and 20%, according to the Opening Rate test.

* * * * *